(12) United States Patent
Emerick et al.

(10) Patent No.: US 9,818,402 B2
(45) Date of Patent: *Nov. 14, 2017

(54) VOICE ASSISTANT SYSTEM

(71) Applicant: Vocollect Healthcare Systems, Inc., Pittsburgh, PA (US)

(72) Inventors: Charles Thomas Emerick, Pittsburgh, PA (US); James R. Logan, Pittsburgn, PA (US); Richard Anthony Bates, Allison Park, PA (US); James Wahl, Escondido, CA (US)

(73) Assignee: Vocollect Healthcare Systems, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/921,211

(22) Filed: Oct. 23, 2015

(65) Prior Publication Data

US 2016/0042737 A1 Feb. 11, 2016

Related U.S. Application Data

(63) Continuation of application No. 13/367,862, filed on Feb. 7, 2012, now Pat. No. 9,171,543, which is a continuation-in-part of application No. 12/536,696, filed on Aug. 6, 2009, now Pat. No. 8,255,225.

(60) Provisional application No. 61/087,082, filed on Aug. 7, 2008.

(51) Int. Cl.
*G10L 15/22* (2006.01)
*G06F 19/00* (2011.01)
*G06F 3/16* (2006.01)

(52) U.S. Cl.
CPC .............. *G10L 15/22* (2013.01); *G06F 3/167* (2013.01); *G06F 19/327* (2013.01); *G06F 19/3418* (2013.01); *G06F 19/363* (2013.01); *G06F 19/3481* (2013.01)

(58) Field of Classification Search
CPC ..... G10L 15/265; G10L 15/00; G10L 13/043; G10L 15/22
See application file for complete search history.

(56) References Cited

U.S. PATENT DOCUMENTS

| | | | | | |
|---|---|---|---|---|---|
| 4,629,015 | A | * | 12/1986 | Fried | A61M 1/16 128/DIG. 13 |
| 5,822,544 | A | * | 10/1998 | Chaco | G06F 19/327 340/286.07 |
| 5,838,223 | A | * | 11/1998 | Gallant | A61G 12/00 340/286.06 |
| 5,853,377 | A | * | 12/1998 | Madsen | G06F 19/3418 600/587 |
| 5,986,568 | A | * | 11/1999 | Suzuki | G06F 19/3418 340/286.07 |

(Continued)

*Primary Examiner* — Douglas Godbold
(74) *Attorney, Agent, or Firm* — Additon, Higgins & Pendleton, P.A.

(57) ABSTRACT

Methods and apparatuses to assist a user in the performance of a plurality of tasks are provided. The invention includes storing at least one care plan for a resident, the care plan defining a plurality of tasks to be performed for providing care to the resident. The method includes capturing speech inputs from the user and providing speech outputs to the user to provide a speech dialog with the user reflective of the care plan. Information is captured with a contactless communication interface and is used for engaging the care plan.

25 Claims, 34 Drawing Sheets

(56) References Cited

U.S. PATENT DOCUMENTS

| | | | |
|---|---|---|---|
| 6,714,913 B2* | 3/2004 | Brandt | G06Q 10/109 700/101 |
| 6,747,556 B2* | 6/2004 | Medema | H04W 64/00 340/286.07 |
| 6,849,045 B2* | 2/2005 | Iliff | A61B 5/0002 128/920 |
| 6,872,080 B2* | 3/2005 | Pastrick | G09B 23/288 434/262 |
| 7,664,657 B1* | 2/2010 | Letzt | G06Q 10/06 705/2 |
| 2003/0182117 A1* | 9/2003 | Monchi | G06F 19/322 704/237 |
| 2003/0208357 A1* | 11/2003 | Hammond | A61F 17/00 704/270 |
| 2006/0200354 A1* | 9/2006 | Ito | G10L 15/26 704/275 |
| 2006/0253281 A1* | 11/2006 | Letzt | G10L 15/30 704/231 |
| 2007/0073168 A1* | 3/2007 | Zhang | A61B 5/0816 600/483 |
| 2007/0167187 A1* | 7/2007 | Rezvani | G10L 15/26 455/550.1 |
| 2007/0219806 A1* | 9/2007 | Yamaki | A61B 17/00 704/275 |
| 2008/0082338 A1* | 4/2008 | O'Neil | A61B 5/145 704/275 |
| 2008/0275739 A1* | 11/2008 | Frick | A61B 5/00 705/3 |
| 2009/0076827 A1* | 3/2009 | Bulitta | 704/275 |
| 2009/0171667 A1* | 7/2009 | Rivera | G06F 19/324 704/275 |
| 2009/0177477 A1* | 7/2009 | Nenov | A61B 5/0002 704/275 |
| 2010/0001838 A1* | 1/2010 | Miodownik | G06F 19/327 340/10.1 |
| 2010/0026817 A1* | 2/2010 | Ryan | G06F 19/3418 348/207.11 |
| 2010/0036676 A1* | 2/2010 | Safdi | G06F 19/321 705/2 |
| 2010/0286490 A1* | 11/2010 | Koverzin | G06F 19/3418 600/301 |

* cited by examiner

You are here ... > Residents > Jane Doe > Toileting

Brown, John
CNA, Meadowlark Lemon Estates
logout

[People Search]

Jane Anne Doe
position: chair
May 13, 3:53 PM

Site
Unit
Residents
Staff
Reports
About

Toileting

I want to... ▶

Physical Functioning - Bowel
*SELECTED: Continence bowel: Usually continent; Level of support bowel: One person physical; Self-performance bowel: Limited assistance.*

Self-performance: [Limited assistance ▼]
Level of support provided: [One person physical assist ▼]
Continence: [Usually continent ▼]

Physical Functioning - Bladder
*SELECTED: Continence bladder: Occasionally incontinent; Level of support bladder: One person physical assist; Self-performance bladder: Limited assistance.*

Self-performance: [Limited assistance ▼]
Level of support provided: [One person physical assist ▼]
Continence: [Occasionally incontinent ▼]

Cautions
*SELECTED: Do not leave unattended in bathroom; High risk for falls.*

☑ Do not leave unattended in bathroom
☑ High risk for falls
☐ Assistance needed for toileting transfer
☐ Notify nurse if dressing soiled or removed

Monitoring
*SELECTED: Scheduled toileting.*

Set up a schedule:
○ None
◉ Scheduled toileting
  ✗ 12:00 PM
  ✗ 2:00 PM
  [Select time... ▼] [AM/PM... ▼] Add another?
○ Bladder training program

Check and change briefs

Starts: [___] 📅
Repeats: [Select time... ▼] [Select time... ▼] [AM/PM... ▼]
Ends: ◉ Never
      ○ Until

☐ Record urine output in ccs

Special Equipment
*No summary found.*
☐ Uses bedside commode or urinal
Uses bedpan: [Does not use bedpan ▼]
Uses catheter: [Does not use catheter ▼]

Briefs
*SELECTED: uses standard briefs.*
○ None
● Uses standard briefs          [Medium ▼]
○ Uses special briefs
☐ Family suppplies incontinense product

Incontinence
*SELECTED: Apply barrier cream to perineal area; Pericare after incontinent episode.*
☑ Uses bedside commode or urinal
[Apply barrier cream to perineal area. ▼]

Ostomy Care
*No summary found.*
☑ Has colostomy bag
☑ Independent with colostome care
☐ Has urostomy bag
☐ Independent with ostomy care
☐ Notify nurse when care required

Custom Notes
*No custom notes.*

Custom Notes
None available.

Add New Note

*Notes longer than 1000 characters will be truncated.*
Expires:
● Never
○ Date: [____] 📅

[Save my changes]   [Do not save my changes]

FIG. 2B

"SELECT ROOM..."

| "DOCUMENT" | "REVIEW" | |
|---|---|---|
| | AMBULATION<br>BATHING<br>DRESSING<br>HYGIENE<br>MEALS<br>MOOD<br>BEHAVIOR<br>POSITIONING<br>RESTORATIVE<br>TOILETING<br>TRANSFERS<br>VITALS | BACKGROUND<br>CARE<br>PAGES<br>REMINDERS<br>UPDATES<br>END OF SHIFT<br>   REPORTS<br>MEDICAL<br>   PRECAUTIONS |

"RECORD"

CLINICAL NOTE
END OF SHIFT REPORTS (Nurses Only)
WELCOME MESSAGE (Nurses Only)

| Self-performance? | Support? |
|---|---|
| Independent | None, Setup |
| Supervison | None, Setup |
| Limited | One-person |
| Extensive | One or Two-person |
| Total | One or Two-person |

HELP
SLEEP
NOISE SAMPLE

"WHO?"

...ARE MY RESIDENTS?
...HAS UPDATES?
...HAS APPOINTMENTS?
...NEEDS VITALS?
...NEEDS BATHING?
...NEEDS CARE?
...NEEDS RESTORATIVE?

"PAGE"

"STAFF MEMBER NAME"
UNIT (for all staff on unit)
SITE (for all staff in facility)
FOR ROOM...

"REVIEW LAST"

WEIGHT    MEALS
URINE      VITALS
BM         FLUIDS

FIG. 4

Ambulation  I want to...

Physical Functioning
*No summary found.*

Self-performance: [Select self-performance...]
Level of support provided: [Select level of support...]

Cautions
*No summary found.*

☐ Shortness of breath
☐ Dizziness
☐ General weakness
☐ Unsteady gait
☐ Fall potential
☐ Check for wander bracelet or anklet Weight bearing:
Left side   [Select weight bearing left side...]
Right side  [Select weight bearing right side...]

Monitoring
*No summary found.*

☐ Uses brace?
☐ Uses splint?
☐ Uses immobilizer?

Special Equipment
*No summary found.*

☐ Uses walker on unit
☐ Uses walker off unit
☐ Uses cane
☐ Uses crutches
☐ Uses sit-to-stand lift for walking
☐ Uses standing frame ☐ Uses wheelchair for distances
☐ Uses wheelchair on unit
☐ Uses wheelchair off unit
☐ Uses electric cart

FIG. 12

Background

Cautions
*No summary found.*
☐ Resident smokes. Do not let resident smoke unattended.

Special Equipment
*No summary found.*
☐ Oxygen equipment needed

Personal Information
*No summary found.*
Lived Alone Prior to Entry
Lifetime Occupation(s)
Marital Status            Select prior living status...
Highest Education Level Completed    Select current marital status...
                          Select education level...

Mental Status
*No summary found.*
☐ Is resident comatose?

Memory
☐ Short-term memory impaired
☑ Long-term memory impaired

Approaches to Mental Status
☐ Requires extra time and patience
☐ Approach calmly
☐ Requires reorientation
☐ Responds to validation

Decision Making
Select decision making skills...

Vision and Hearing
*No summary found.*

I want to...

FIG. 13A

Vision

Select vision ability... ▼

Left Eye
☑ Blind
☑ Artificial
☑ Requires use of glasses, contact lenses, etc.

Right Eye
☐ Blind
☑ Artificial

Routines
*No summary found.*

Sleep Patterns
☑ Stays up late at night (e.g., after 9pm)
☑ Naps regularly during day for at least 1 hour
☑ Sleeps all night
☑ Exhibits wandering behavior
☑ Elevate head of bed

Rest Patterns
☑ Morning
☑ Afternoon
☑ Evening

Speech
*No summary found.*

Primary Language
Select primary language... ▼

Speech
Select speech quality... ▼

Hearing
Select hearing ability... ▼

Left Ear
☑ Hearing Aid
☑ Deaf

Right Ear
☐ Hearing Aid
☑ Deaf

Customary Routine
Stays busy with the following activities:

☐ Hobbies
☑ Reading
☑ Music
☑ Games
☑ Family members visit regularly

☑ Welcomes pet visits
☑ Fixed routine
☐ TV
☑ Welcomes day care children

Secondary Language
Select secondary language... ▼

Ability to understand others
Select ability to understand... ▼

FIG. 13B

Bathing                                                             I want to... ▼

Physical Functioning
*No summary found.*
Self-performance:     [Select self-performance... ▼]
Level of support provided:  [Select level of support ▼]

Cautions
*No summary found.*
☐ Assistance needed for transfer
☐ Uses special shampoo
☐ Uses special soap
☐ Wrap cast in plastic before bathing
☐ Water temperature no higher than 100 F
☐ Do not wash hair

Monitoring
*No summary found.*
☐ Before bathing, check entire body and report warm, discolored or open skin areas
☐ Test and reapply bed or chair alarm

Scheduled care:

|          | Sunday  | Monday  | Tuesday | Wednesday | Thursday | Friday  | Saturday |
|----------|---------|---------|---------|-----------|----------|---------|----------|
| Nail care| -Shift- | -Shift- | -Shift- | -Shift-   | -Shift-  | -Shift- | -Shift-  |
| Shower   | -Shift- | -Shift- | -Shift- | -Shift-   | -Shift-  | -Shift- | -Shift-  |
| Bed bath | -Shift- | -Shift- | -Shift- | -Shift-   | -Shift-  | -Shift- | -Shift-  |
| Tub bath | -Shift- | -Shift- | -Shift- | -Shift-   | -Shift-  | -Shift- | -Shift-  |

FIG. 14

Dressing

I want to... ▼

Physical Functioning
*No summary found.*

Self-performance: [Select self-performance...]
Level of support provided: [Select level of support...]
☐ Selects own clothes
☐ Able to make needs known
Assist with extremities: ☐ Upper ☐ Lower

Cautions
*No summary found.*

Dress dependent side first. [Select side...]
☐ Follow hip precautions

Monitoring
*No summary found.*

☐ Before dressing, check entire body and report warm, discolored or open skin areas
☐ After undressing, check entire body and report warm, discolored or open skin areas
☐ Test and reapply bed or chair alarm Dress resident            ☐ Day ☐ Evening ☐ Night
Undress resident          ☐ Day ☐ Evening ☐ Night
Lay out clothing          ☐ Day ☐ Evening ☐ Night

Special Equipment
*No summary found.*

☐ Has artificial limb?

Uses dressing aids:
☐ Reacher
☐ Sock aid
☐ Dressing stick
☐ Long-handled shoe horn Wears:
☐ Hip pacs
☐ Adaptive clothing
☐ Adaptive shoes
☐ Knee-high stockings
☐ Thigh-high stockings
☐ Non-skid socks
☐ Sports bra

FIG. 15

Personal Hygiene | I want to... ▼

Physical Functioning
*No summary found.*

Self-performance: [Select self-performance...]
Level of support provided: [Select level of support...]

Cautions
*No summary found.*

☐ Rinse dentures thoroughly after soaking
☐ Report any mouth wash that contains alcohol
☐ Monitor and report mouth ulcers
☐ Check with nurse before grooming

Monitoring
*No summary found.*

Denture care
On [Select shift...] shift, [ ] times

Tooth care
On [Select shift...] shift, [ ] times

Total mouth care
On [Select shift...] shift, [ ] times

Apply vaseline to lips
On [Select shift...] shift, [ ] times

FIG. 16A

Special Equipment
*No summary found*

Upper dentures: [Select...]
Lower dentures: [Select...]
☐ Assist with inserting dentures
☐ Use denture adhesive
☐ Soak dentures in cleanser at bedtime
☐ Use easy gel mouth care product
☐ Use toothettes as needed
☐ Use glycerin swabs as needed
Shaving: [Select razor type...]

AM/PM/Extra Care
*No summary found*

| | AM CARE | PM CARE | EXTRA CARE | | |
|---|---|---|---|---|---|
| | Select shift... | Select shift... | Day | Evening | Night |
| Apply hand lotion | ☐ | ☐ | ☐ | ☐ | ☐ |
| Brush hair | ☐ | ☐ | ☐ | ☐ | ☐ |
| Check and clean glasses | ☐ | ☐ | ☐ | ☐ | ☐ |
| Check hearing aid | ☐ | ☐ | ☐ | ☐ | ☐ |
| Glasses at bedside | ☐ | ☐ | ☐ | ☐ | ☐ |
| Hearing aid kept in room | ☐ | ☐ | ☐ | ☐ | ☐ |
| Hearing aid kept on med cart | ☐ | ☐ | ☐ | ☐ | ☐ |
| Remove dentures | ☐ | ☐ | ☐ | ☐ | ☐ |
| Remove hearing aid | ☐ | ☐ | ☐ | ☐ | ☐ |
| Remove TED stockings and provide foot care | ☐ | ☐ | ☐ | ☐ | ☐ |
| Replace dentures | ☐ | ☐ | ☐ | ☐ | ☐ |
| Replace hearing aid | ☐ | ☐ | ☐ | ☐ | ☐ |
| Shave with razor | ☐ | ☐ | ☐ | ☐ | ☐ |
| Use body cream or lotion | ☐ | ☐ | ☐ | ☐ | ☐ |
| Wig care | | | ☐ | ☐ | ☐ |

FIG. 16B

Meals

I want to... ▼

Physical Functioning
No summary found.

Self-performance: [Select self-performance...]
Level of support provided: [Select level of support...]

Cautions
No summary found.
☐ NPO at all times
☐ No straw
☐ Chewing difficulty
☐ Swallowing problem
Thickened liquids:
  [Does not use thickened liquids]
☐ Aspiration precautions
☐ Keep head of bed raised 30 degrees or higher after meals

Daily fluid restriction
Day
Evening
Night

Monitoring
SELECTED: Record meal intake in percent.
☑ Record meal intake in percent
☐ Record fluid intake in CCs

Clear liquids
for [    ] hours, starting at [Select time...] [AM/PM...] on [    ]

NPO
for [    ] hours, starting at [Select time...] [AM/PM...] on [    ]

Feeding tube:
  [Does not use feeding tube]
☐ Uses IV
☐ No water pitcher at bedside
☐ Eats better alone in dining room
Clean pockets between gums and cheeks:
☐ After meals
☐ After snacks

FIG. 17A

Offer beverage

Starts: [____] [Select time...] [AM/PM...]

Repeats: [Does not repeat]

Ends: ● Never
       ○ Until

Snacks:
☐ Requires snacks/supplements for medical reasons
Type: [Select a snack type...]

Special Equipment
*No summary found.*

☐ Uses special utensils
☐ Uses divided plate
☐ Provide wash cloth before and after eating

Diet Options
*No summary found.*

Diet Type:
● None
○ House
○ Mechanical soft
○ Pureed

☐ Clear liquids
☐ No added salt
☐ No concentrated sweets
☐ Low residue diet

Eating Locations
*No summary found.*

Breakfast: [Selec: breakfast location...]
Lunch: [Selec: lunch location...]
Dinner: [Selec: dinner location...]

Beverage Preferences
*No summary found.*

☐ Prefers ice in beverages      ☐ Prefers orange juice        ☐ Prefers milk
☐ Prefers water                 ☐ Prefers cranberry juice     ☐ Prefers coffee
☐ Prefers apple juice           ☐ Prefers ginger ale          ☐ Prefers tea

FIG. 17B

Medical Precautions

I want to... ▼

Cautions
*No summary found.*

Blood Pressure
☐ Resident had right mastectomy
☐ Resident had left mastectomy
☐ Resident had double mastectomy

Other
☐ Neuro Checks
☐ Has had recent surgery - check with nurse
☐ Seizure precautions - notify nurse

General Precautions
*No summary found.*

☐ Do not hospitalize       ☐ C-diff contact
☐ No antibiotics           ☐ Stool contact
☐ Comfort measures only    ☐ Droplet
☐ Has hospice care

Isolation Precautions
*No summary found.*

☐ Respiratory
☐ Sputum contact
☐ Airborne

VRE Contact
Select VRE contact...

MRSA Contact
Select MRSA contact...

FIG. 18

Mood/Behavior

I want to... ▼

Monitoring
*No summary found*
☐ Record mood
☐ Record behavior

Mood
*No summary found*

If resident displays loss of interest
☐ Encourage resident to socialize with other residents
☐ Focus on resident's strengths and past successes
☐ Provide tasks and activities specific to the resident's interests
☐ Reminisce with resident Add new intervention: [        ]

If resident displays sad, apathetic, or anxious appearance
☐ Approach the resident from the front
☐ Approach the resident in a calm, quiet manner
☐ Call the resident by name
☐ Help resident express feelings
☐ Offer snack or beverage
☐ Offer toileting
☐ Provide tasks and activities specific to the resident's interests
☐ Speak slowly
☐ Talk socially about non-care issues Add new intervention: [        ]

If resident displays sleep-cycle issues
☐ Encourage exercise and activity early in the day
☐ Follow bedtime rituals
☐ Keep noise level low
☐ Limit caytime naps
☐ Offer snack or beverage
☐ Offer toileting

FIG. 19A

Add new intervention:

If resident displays verbal expressions of distress
☐ Approach the resident from the front
☐ Approach the resident in a calm, quiet manner
☐ Call the resident by name
☐ Do not interrupt or rush the resident
☐ Give simple choices
☐ Speak slowly
☐ Use simple words and sentences Add new intervention:

Custom Notes: Mood
None available.

Add New Note

Expires:
○ Never
○ Date:

Behavior
No summary found.

If resident displays physically abusive behavior
☐ Approach the resident from the front
☐ Approach the resident in a calm, quiet manner
☐ Ask another caregiver to help with resident
☐ Call the resident by name
☐ Speak slowly and calmly Add new intervention:

FIG. 19B

If resident resists care
- ☐ Clearly explain care
- ☐ Consider having caregiver of different gender assist
- ☐ Give choice of times for care to be performed
- ☐ Leave resident and return later
- ☐ Provide opportunity for resident to make own choices
- ☐ Talk with resident about non-care issues before completing task Add new intervention: [          ]

If resident displays socially inappropriate/disruptive behavior
- ☐ Have resident return to room
- ☐ Offer snack or beverage
- ☐ Offer toileting
- ☐ Provide tasks and activities specific to the resident's interests
- ☐ Reassure resident
- ☐ Redirect resident Add new intervention: [          ]

If resident displays verbally abusive behavior
- ☐ Do not argue with resident
- ☐ Focus on subjects that are not upsetting
- ☐ Have resident return to room
- ☐ Leave resident and return later
- ☐ Redirect resident
- ☐ Speak calmly Add new intervention: [          ]

If resident wanders
- ☐ Accompany resident when leaving unit
- ☐ Offer snack or beverage
- ☐ Offer toileting
- ☐ Provide safe place for resident to wander
- ☐ Provide tasks and activities specific to the resident's interests Add new intervention: [          ]

FIG. 19C

Positioning

Physical Functioning
No summary found.
Self-performance: [Select self-performance...]
Level of support provided: [Select level of support...]

Cautions
No summary found.
☐ High risk for falls
☐ Balance problems

Avoid Pressure Ulcers
☐ Limit sitting out of bed to meals only
☐ Float heels to avoid pressure
Keep off:
☐ Left          ☐ Right          ☐ Back
Avoid pressure:
☐ Back          ☐ Heels          ☐ Upper extremities
☐ Neck          ☐ Elbows         ☐ Lower extremities

Mobility
Foot drop:    ☐ Left  ☐ Right
Paralysis:    ☐ Left  ☐ Right
Weakness:     ☐ Left  ☐ Right
☐ Can wheel self
☐ Contracture
☐ Limited range of motion I want to... ▼

FIG. 20A

Hip and Joint Cautions
☐ Uses hip chair
☐ No bending hip past 90 degrees
☐ No twisting ☐ Keep knees apart
☐ No pigeon-toed position

Monitoring
*No summary found.*

Reposition resident:
[Select time ▼] [AM/PM ▼] [Add another?]
☐ Test and reapply bed or chair alarm

Multi-PODUS Boot
Apply/remove:    ☐ Day ☐ Evening ☐ Night

Heel protector
Apply/remove:    ☐ Day ☐ Evening ☐ Night

Special Equipment
*No summary found.*

☐ Pillows
☐ Bed cradle
☐ Air mattress
☐ Wheelchair
☐ Broda chair
☐ Recliner

☐ Trapeze
☐ Wedges
☐ Footboard
☐ Foot cradle
☐ Overlay mattress in bed

Rails: [Select rails to put up... ▼]

Safety and Emergency
☐ Foot rests removed
☐ Uses perimeter mattress sleeve
☐ Put mat in place beside bed
☐ Ensure signal cord within reach at all times
☐ Half-privacy door

Bed Mobility
*No summary found.*
☐ Rolls
☐ Elevate head of bed
☐ Uses low bed

FIG. 20B

Transfers

Physical Functioning
*No summary found.*

Self-performance: [Select self-performance...]
Level of support provided: [Select level of support...]

Cautions
*No summary found.*

Pain cautions
- ☐ Head
- ☐ Neck
- ☐ Back
- ☐ Abdomen
- ☐ Ribs
- ☐ Wound
- ☐ General arthritic pain

- ☐ Left foot
- ☐ Left leg
- ☐ Left hip
- ☐ Left arm
- ☐ Left hand

- ☐ Right foot
- ☐ Right leg
- ☐ Right hip
- ☐ Right arm
- ☐ Right hand

Monitoring
*No summary found.*

☐ Test and reapply bed or chair alarm

Special Equipment
*No summary found.*

- ☐ Cane
- ☐ Wheelchair
- ☐ Electric wheelchair or cart
- ☐ Gait belt
- ☐ Pivot disc
- ☐ Sliding board
- Rails: [Select rails to put up...]

Walker
- ☐ Rolling walker
- ☐ Three-wheel walker
- ☐ Contact guard with walker
- ☐ Platform device on walker

Lift
- ☐ Standing lift
- ☐ Sling lift

Devices
- ☐ Lap tray
- ☐ Pummel cushion
- ☐ Grab bars

I want to... ▼

FIG. 21

Vitals and Weight

I want to... ▼

Cautions
*No summary found.*

☐ Do not take BP from right arm
☐ Do not take BP from left arm
☐ Do not take BP from either arm
☐ Use thigh for BP
Temperature location: [Select location...]

Monitoring
*No summary found.*

All Vitals

Starts: [___] [Select time...] [AM/PM...]
Repeats: [Does not repeat]
Ends: ● Never
      ○ Until

Blood Pressure

Starts: [___] [Select time...] [AM/PM...]
Repeats: [Does not repeat]
Ends: ● Never
      ○ Until

VOICE ASSISTANT SYSTEM

CROSS-REFERENCE TO RELATED APPLICATIONS

The present application claims the benefit of U.S. patent application Ser. No. 13/367,862 for a Voice Assistant System filed Feb. 7, 2012 (and published May 31, 2012 as U.S. Patent Application Publication No. 2012/0136667), now U.S. Pat. No. 9,171,543, which is a continuation-in-part of U.S. patent application Ser. No. 12/536,696 for a Voice Assistant System filed Aug. 6, 2009 (and published Feb. 11, 2010 as U.S. Patent Application Publication No. 2010/0036667), now U.S. Pat. No. 8,255,225, which claims the benefit of U.S. Patent Application No. 61/087,082 for a Voice Assistant System filed Aug. 7, 2008. Each of the foregoing patent applications, patent publications, and patents is hereby incorporated by reference in its entirety.

U.S. patent application Ser. No. 12/879,704 for a Voice Assistant System for Determining Activity Information filed Sep. 10, 2010 (and published Feb. 17, 2011 as U.S. Patent Application Publication No. 2011/0040564), now U.S. Pat. No. 8,521,538, is also a continuation-in-part of U.S. patent application Ser. No. 12/536,696. Each of the foregoing patent applications, patent publication, and patent is hereby incorporated by reference in its entirety.

FIELD OF THE INVENTION

This invention generally relates to the use of speech or voice technology in a work environment to facilitate a variety of tasks.

BACKGROUND

Speech or voice technology, in the form of speech recognition, is used in a variety of different environments to facilitate the completion of work or various tasks. One example of a specific use for a voice-directed system is the direction of a worker to perform various tasks and to collect data associated with the task execution.

In a typical voice-directed work system, the worker wears a mobile computer having voice or speech capabilities. The computer is worn on the body of a user, such as at their waist, and a headset device connects to the mobile computer, such as with a cable or possibly in a wireless fashion. In another embodiment, the mobile computer might be implemented directly in the headset. The headset includes one or more speakers for playing voice and speech instructions and other audio outputs that are generated or synthesized by the mobile computer to direct the work of the user and to confirm the spoken words of the user. The headset also has a microphone for capturing the speech inputs of the user to determine the commands spoken by the user and to allow the entry of data using the user's speech and speech recognition. Through the headset and speech recognition and text-to-speech capabilities of the mobile computer, workers are able to receive voice instructions or questions about their tasks, to receive information about their tasks, to ask and answer questions, to report the progress of their tasks, and to report various working conditions, for example.

The mobile and/or wearable computers allow the users that wear or use them to maintain mobility at a worksite, while providing the users with desirable computing and data-processing functions. Generally, such mobile computers often provide a wireless communication link to a larger, more centralized computer system that directs the work activities of a user within a system and processes any user speech inputs, such as collected data, in order to facilitate the work. An overall integrated system may utilize a central system that runs a variety of programs, such as a program for directing a plurality of mobile computers and their users in their day-to-day tasks. The users perform manual tasks and enter data according to voice instructions and information they receive from the central system, via the mobile computers. This process is generally referred to as voice-directed work as the user takes specific direction from the central system and their computer like they might take direction from a manager or supervisor or from reading a work order or to-do list.

The mobile computers provide a significant efficiency in the performance of a user's tasks. Specifically, using such mobile computers, the work is done virtually hands-free without equipment to juggle or paperwork to carry around. However, while existing speech systems provide hands-free operations, voice-directed work may be overly structured for some users and for some work environments. Various work environments require that the worker know what they are doing in any particular task, and thus they do not have to be told how to specifically perform a particular task or what order to handle multiple tasks. Directing work in those environments in an automatic fashion, as is the case with typical voice-directed work, is not suitable and can be overbearing.

One such environment that requires greater worker flexibility is the work environment in a nursing home or assisted living facility. In such facilities, nurses create care plans for all of the residents, and the care plans define the different tasks to be performed by the nurses or by certified nursing assistants ("CNAs") or other care providers for the residents. In particular, each CNA, for example, has to be aware of and accountable for the tasks in the care plans of the residents that are assigned by the nurses to that CNA. Generally, the CNAs know how to perform the various tasks, such as bathing a resident, and do not need to be told by the central system how to perform the task. Furthermore, the CNA may also control the order in which they choose to address a multitude of tasks and thus take advantage of certain efficiencies in their workflow. The workflow will often depend upon the CNAs environment, their location, the urgency of the task and various other factors, and thus they have great flexibility in performing their work. For example, a CNA may want to first take the vitals of an assigned resident if the CNA has immediate access to the proper equipment for taking the vitals, and then bathe the resident. Or vice versa.

Therefore, the rigid approach of traditional voice-directed work environments, while suitable for some work, would not be suitable in a resident or patient care environment. In fact, the CNA is more likely to be hindered by a computer or device that rigidly directs the CNA to perform their tasks in a certain order or to ignore their own judgment with respect to an efficient workflow.

Furthermore, in traditional voice-directed work, the back and forth of the speech is usually constant as the worker is directed to a task, confirms completion of the task, and then is immediately directed to the next task. The central system controls the dialog and thus, to some extent, controls the worker. As may be appreciated, in a patient or resident care facility, a CNA or other worker will often be speaking with the resident or other staff in the course of their day. As such, it would be disruptive to have to constantly be interfacing with an aggressive voice-directed system while also trying to converse with another person. Furthermore, many of the residents in such facilities are older and may find it disturbing and confusing when their CNA or other attendee has to speak at inappropriate times to maintain their workflow because the voice-directed system is controlling the dialog.

A voice assistant system has been developed for assisting CNAs and other care providers implementing a speech dialog. The AccuNurse® Program, available from Vocollect Healthcare Systems, Inc. of Pittsburgh, Pa., provides a speech-based system to assist the care provider in implementing care plans for residents in care facilities. Such a system is described in U.S. patent application Ser. No. 12/536,696 entitled "Voice Assistant System". While such a system provides a desirable relationship between the care provider and the speech dialog, there is a further desire to improve on such a system to make it less intrusive or disruptive for the care provider and resident. Particularly, since the care provider will be speaking to the system in the presence of a resident for entering information and data into the system, certain new situations may be disturbing or confusing to a resident or may appear to be impersonal with respect to the care provided. Therefore, a need exists to improve upon the system in certain situations to mitigate any confusion or undesirable experiences by a resident.

A need therefore exists to further improve existing systems and still facilitate a more efficient work environment without being overly rigid and overly domineering. There is further a need for maintaining periods of silence at certain times while still being able to proceed with tasks and provide care. Still further, there is a need to ensure that the dignity of the resident is respected and confusion avoided in providing speech-assisted care.

SUMMARY

Embodiments of the invention provide for a method and apparatus to assist a user in the performance of a plurality of tasks. In one embodiment, the method comprises storing a care plan in a voice assistant carried by a user, the care plan defining a plurality of tasks to be performed by the user as part of a workflow. The method further comprises capturing speech input from the user with a mobile device, determining, from the speech input, a selected interaction with a care plan, and, in response to the selected interaction, providing a speech dialog with the user through the mobile device that is reflective of the care plan. In providing care to a resident using a mobile device, individualized care plans for a plurality of residents are stored and maintained. As part of the speech dialog, speech inputs are captured from the user through the mobile device, and speech outputs are provided to a user also through the mobile device. The speech dialog is reflective of a care plan for a resident. A contactless communication interface is also used in combination with the speech dialog for capturing information in a silent fashion for assisting in the provision of care. In one embodiment, the captured information is used for engaging the care plan for a resident. Alternatively, the captured information is used to assist a care provider to further care for a resident such as to associate an item with a resident.

These and other advantages will be apparent in light of the following figures and detailed description.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

FIGS. 2A-2B are an example of a care plan for a resident that may be generated via a nursing workstation in the voice assistant system of FIG. 1A consistent with the principles of the present invention;

FIG. 4 is one example of a document that may be physically carried by a user to interact with the voice assistant system of FIG. 1A consistent with the principles of the invention;

FIG. 12 is an example of another care plan for a resident similar to FIGS. 2A-2B;

FIGS. 13A-13B are examples of another care plan for a resident similar to FIGS. 2A-2B;

FIG. 14 is an example of another care plan for a resident similar to FIGS. 2A-2B;

FIG. 15 is an example of another care plan for a resident similar to FIGS. 2A-2B;

FIGS. 16A-16B are examples of another care plan for a resident similar to FIGS. 2A-2B;

FIGS. 17A-17B are examples of another care plan for a resident similar to FIGS. 2A-2B;

FIG. 18 is an example of another care plan for a resident similar to FIGS. 2A-2B;

FIGS. 19A-19B-19C are examples of another care plan for a resident similar to FIGS. 2A-2B;

FIGS. 20A-20B are examples of another care plan for a resident similar to FIGS. 2A-2B;

FIG. 21 is an example of another care plan for a resident similar to FIGS. 2A-2B; and FIGS. 22A-22B are examples of another care plan for a resident similar to FIGS. 2A-2B.

Figure 1A:
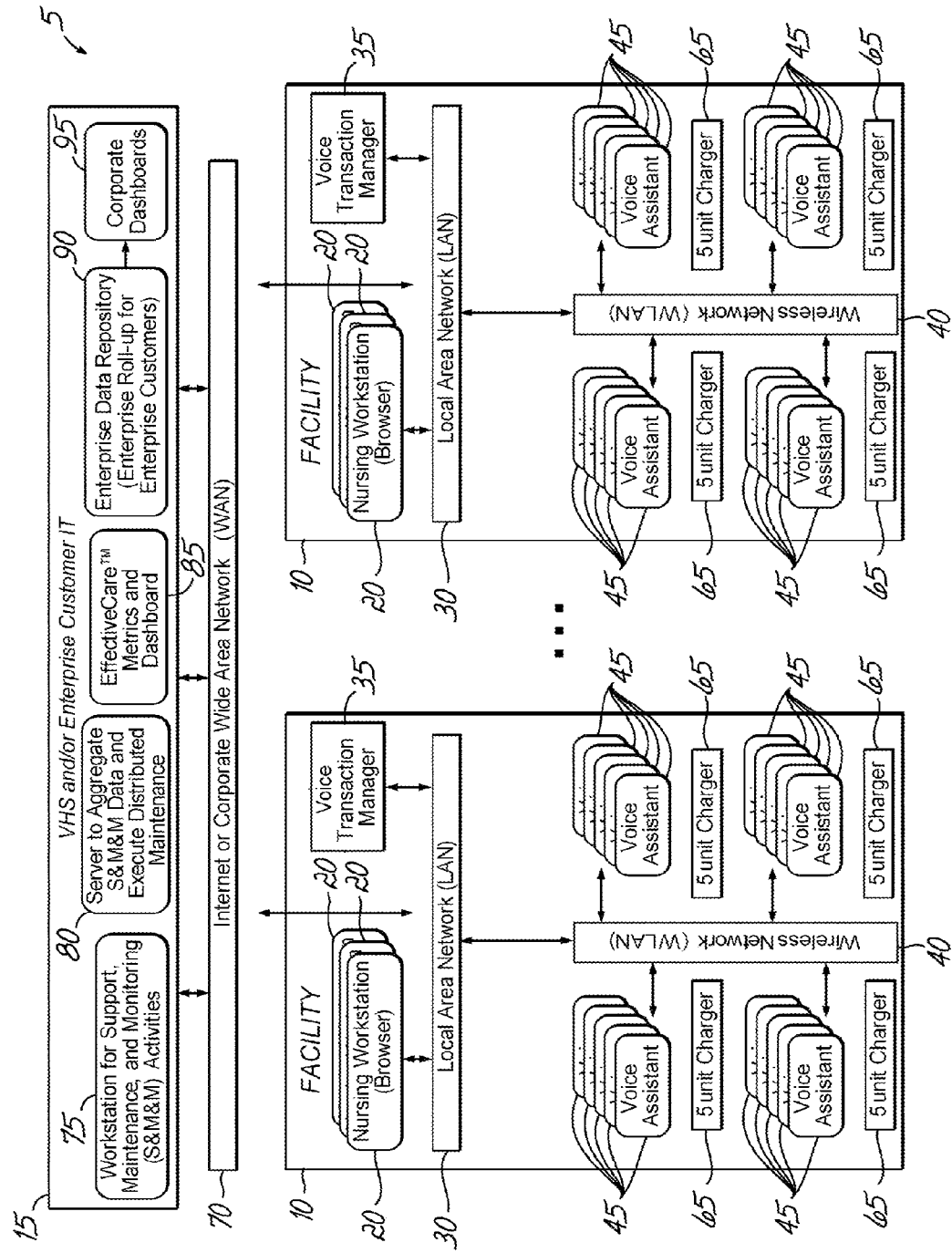
FIG. 1A is a block diagram of a distributed implementation of a voice assistant system consistent with the principles of the present invention.

It should be understood that the appended drawings are not necessarily to scale, presenting a somewhat simplified representation of various features illustrative of the basic principles of embodiments of the invention. The specific design features of embodiments of the invention as disclosed herein, including, for example, specific dimensions, orientations, locations, and shapes of various illustrated components, as well as specific sequences of operations (e.g., including concurrent and/or sequential operations), will be determined in part by the particular intended application and use environment. Certain features of the illustrated embodiments may have been enlarged or distorted relative to others to facilitate visualization and clear understanding.

DETAILED DESCRIPTION

Embodiments of the invention provide a voice assistant system for assisting a user. In some embodiments, the voice assistant assists a CNA or other care provider with performing a variety of tasks during the CNA's work shift. It is understood that the voice assistant system may be used in other work environments as well. Consistent with embodiments of the invention, the CNA may engage the inventive voice assistant via a main menu in the form of Situational Awareness Questions, and the CNA may be provided with a speech dialog that answers the various questions and/or provides other information. By doing so, the voice assistant system assists the CNA by providing information that is more pertinent to the situation the CNA is encountering, generally reducing the rigidity of voice-directed work. As will be readily understood, while a CNA is set forth herein as a particular person to utilize the present invention in a care facility, embodiments of the invention are not limited to a particular user. Alternative users of various embodiments of the invention are anticipated and understood to be beneficiaries of the features disclosed herein. For example, a physician, nurse, and/or other caregiver in a facility may use various embodiments of the invention.

The CNA may also use a speech command, and the CNA may be provided with a speech dialog associated with the command to assist the CNA with the execution of a task. Moreover, the voice assistant system may also analyze data received from the CNA and provide a speech dialog at the point of care that may assist the CNA in the efficiency and accuracy of their work. Furthermore, the voice assistant system may provide reminders, pages and/or other indications (e.g., "all clear" indications or messages) to assist the CNA in managing their workflow. In one embodiment, the voice assistant system may be and/or may incorporate or include the AccuNurse® software and/or hardware offered by the assignee of this application, Vocollect Healthcare Systems, Inc. ("VHS") of Pittsburgh, Pa.

Those of ordinary skill in the art will appreciate that the voice assistant system described herein seeks to assist the CNAs with their tasks in a more flexible and fluid manner by providing audible tones, messages regarding instructions, information in response to the Situational Awareness Questions, and/or assistance with execution of the tasks and analysis of data via the commands, as opposed to rigid, conventional voice-directed systems that order users to perform specific tasks in a set order, set flow, set manner, and/or at a set time. Indeed, voice-directed work typically dictates each task to be performed, the order they are performed in, and when they are to be performed, whereas the voice assistant system described herein allows a CNA to decide what tasks to perform, the order to perform them, and when to perform them, with care plans providing guidance. As such, the voice assistant complements the CNA's task choices and provides assistance via a voice dialog as needed to the CNA (e.g., when the CNA initiates the assistance, when the CNA should be informed of something such as a page). In other words, in conventional voice-directed work systems, the system is typically in charge and the users follow the orders, whereas in a voice assistant system the CNA is in charge and the system follows orders to provide assistance as needed.

Turning now to the Drawings, wherein like numbers denote like parts throughout the several figures, FIG. 1A is a diagrammatic illustration of a voice assistant system 5 that may be in the form of a distributed computing system, with computing activities associated with at least one onsite nursing home or assisted living facility as at 10. The nurses, CNAs, and residents of a facility are typically physically located at the facility 10, while centralized support and management capabilities for the voice assistant system 5 may be provided by an offsite VHS department and/or by an onsite enterprise customer IT department 15.

Figure 1B:
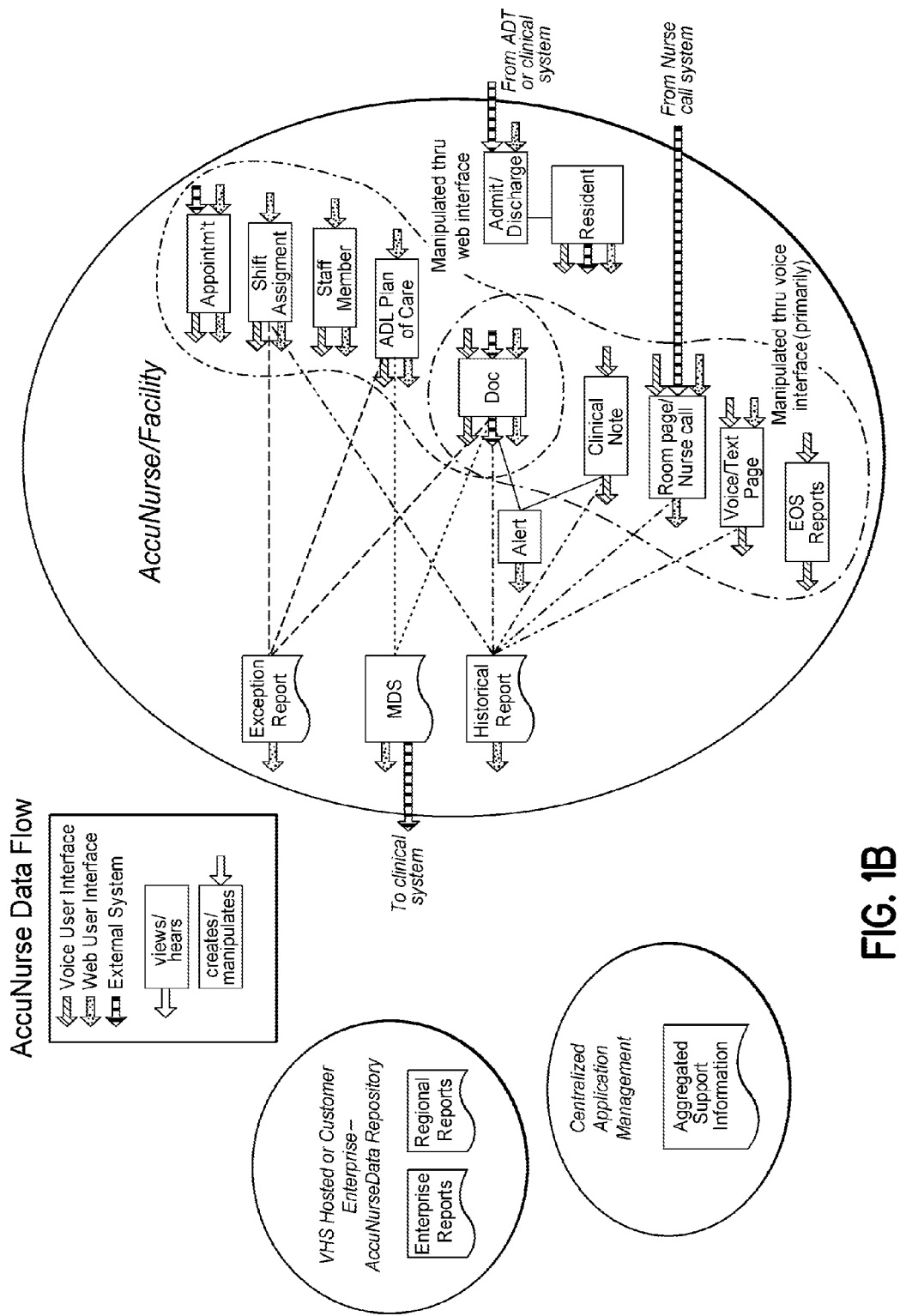
FIG. 1B is a block diagram of data flow in the voice assistant system of FIG. 1A consistent with the principles of the present invention.

As illustrated, the voice assistant system 5 may include more than one facility 10, and each facility 10 may be subdivided into a plurality of units. All of the units may be referred to as a site, but will generally be referred to as the facility 10 for simplicity, unless otherwise stated. Also for simplicity, the discussion will primarily focus on a single facility 10 and its respective nursing workstation 20, voice assistant 45, and charger 65 (discussed further hereinbelow), even though a plurality of these items are illustrated in FIGS. 1A-1B. Those of ordinary skill in the art will appreciate, however, that embodiments of the invention may apply equally to the other facilities (including other nursing workstations, other voice assistants, and other chargers) in the voice assistant system 5. Furthermore, the discussion of embodiments of the invention will be from the perspective of a single CNA utilizing the voice assistant 45 for simplicity, but those of ordinary skill in the art will appreciate that each CNA and/or each nurse may have a voice assistant 45.

Turning to the facility 10, at least one care plan is generated by a nurse or other qualified personnel for each resident at the facility 10. In the description of the invention, the persons receiving care are generally referred to as residents, as they may be resident in or living in a care facility, such as a long term care facility. However the invention is applicable to other people or patients as well who might be in a care facility more temporarily but still may have a care plan associated with them. There the term "resident" as used herein is not meant to be limiting and includes other persons or patients receiving care from a care provider. In one feature of the present invention, interactive care plans are created and maintained for interacting with the voice assistant 45. As such, the care plans may be accessible through the nursing work station 20. The information of the care plans may be accessed by the voice assistants 45 to assist the CNAs, by voice, and a speech dialog in the various tasks associated with the care plans. Advantageously, it is believed that this is a significant improvement over the use of written care plans that are typically located in various binders at a nursing station. It is worth noting that the CNAs may not be authorized to generate and/or change care plans, but the CNAs can view and perform the tasks in the care plans. To generate and/or revise care plans, the facility 10 may include at least one nursing workstation 20 and a nurse or other qualified personnel associated therewith may generate and/or revise a care plan as needed via a graphical user interface, such as an application displayed via a web browser, associated with the nursing workstation 20 (see FIG. 1B). Specifically, the application displayed may display a variety of information for the nurse to select, including pull-down menus, boxes, etc. Using the pull-down menus, boxes, etc., the nurse may generate and/or revise a care plan as needed. FIGS. 2A and 2B illustrate an exemplary care plan 25 for toileting for a resident named Jane Doe as displayed in the application. Specifically, FIGS. 2A and 2B illustrate an exemplary care plan 25 prior to a nurse saving the changes to the toileting care plan. Various other care plans may exist as well. For example, the care plan of FIG. 12 is directed to Ambulation of the Resident; FIGS. 13A-13B to Background Information; FIG. 14 is directed to Bathing; FIG. 15 to Dressing; FIGS. 16A-16B to Personal Hygiene; FIGS. 17A-17B to Meals; FIG. 18 to Medical Precautions; FIGS. 19A-19C to Mood/Behavior; FIGS. 20A-20B to Positioning; FIG. 21 to Transfers; and FIGS. 22A-22B to Vitals and Weight. However, one of ordinary skill in the art will appreciate that there may be additional care plans for other tasks and/or information. Each care plan may have various menus, boxes, and other selectable fields for entering or selecting information and parameters for the care plan. The care plans may be displayed via the application in the web browser, and the care plans may direct the workflow of the CNA via the voice assistant 45 (discussed further hereinbelow). The care plans for a particular resident may determine what tasks the CNA must perform for that resident during the shift.

Furthermore, the nursing workstation 20 may also be utilized to generate and/or update work assignments for the CNAs. For example, before the start of the shift of a particular CNA, the nurse or other qualified personnel in the facility 10 (or unit thereof) may set up and/or update the work assignment for the CNA via the nursing workstation 20. As such, the nurse or qualified personnel may set up and/or update a work assignment for the CNA to include an assignment of residents to that CNA for a shift or appointments associated with the CNA (including an appointment with a resident), as well as make changes to a care plan for a resident. The nurse or other qualified personnel may also print out an exception report from the nursing workstation 20 that indicates the tasks that still need to be performed by a CNA.

The nursing workstation 20 may represent practically any type of computer, computer system, appliance, or other programmable electronic device. The nursing workstation 20 may also be capable of functioning as a client and/or server or may be implemented using one or more networked computers, e.g., in a cluster or other distributed computing system. In some embodiments, the nursing workstation 20 may be similar to a client computer.

Along with the web browser, the nursing workstation 20 may also include an operating system, at least one processor such as a central processing unit (CPU), a memory, mass storage, a user interface, a network interface, and/or routines that are configured to be executed to implement the embodiments of the invention, whether implemented as part of an operating system or a specific application, component, program, object, module or sequence of instructions, or even a subset thereof, which will be referred to herein as "computer program code", or simply "program code." Program code typically comprises one or more instructions that are resident at various times in various memory and storage devices in a computer, and that, when read and executed by one or more processors in a computer, cause that computer to perform the steps necessary to execute steps or elements embodying the various aspects of the invention.

The information associated with at least one care plan may be transmitted (e.g., in digital form) from the nursing workstation 20 (e.g., using the network interface) via a local area network (LAN) 30 to a voice transaction manager 35. Each facility 10 may have at least one voice transaction manager 35 to store the care plans and facility configuration information. Specifically, the voice transaction manager 35 sits on the LAN 30 and may represent and/or include practically any networked appliance, device, or computer as described hereinabove in connection with the nursing workstation 20. As such, and in some embodiments, the voice transaction manager 35 may include a web server and/or a database server as is known to a person of ordinary skill in the art. Thus, the voice transaction manager 35 may include at least one database for storing the data, which may in turn be transmitted from the voice transaction manager 35 to the nursing workstation 20.

Furthermore, in one embodiment of the invention, Solaris may be utilized as the native operating system in the voice transaction manager 35, but no explicit operating system dependencies may be required for the web server and/or the database server. Java may be utilized as the native programming language of the voice transaction manager 35, and the voice transaction manager 35 may be implemented and managed using conventional Internet technologies. The voice transaction manager 35 may also function as backup in case of data loss. From the perspective of the nurses and CNAs, the voice transaction manager 35 may not require onsite IT maintenance beyond turning the power on and off. Furthermore, a type of network other than the LAN 30 may alternatively be utilized to transmit data from the nursing workstation 20 to the voice transaction manager 35.

Next, the information and data associated with at least one of the care plans in the voice transaction manager 35 may be transmitted (e.g., in digital form) from the voice transaction manager 35 (e.g., using the network interface) through the LAN and via wireless network 40 (e.g., a wireless local area network, or "WLAN") to at least one voice assistant 45. The LAN and WLAN are bridged by standard networking circuitry which is generally transparent to the voice transaction manager 35. Data may also be transmitted from the voice assistant 45 to the voice transaction manager 35, for example, for storage and/or processing at the voice transaction manager 35.

The voice assistant 45 may include three separate portions, including a headset portion 50 (e.g., including a microphone 51, one or more earpieces 53, and one or more speakers 57), a device portion 55 and a connecting portion 60. In some embodiments, the connecting portion 60 may be a cable or a wireless link.

Figure 3:
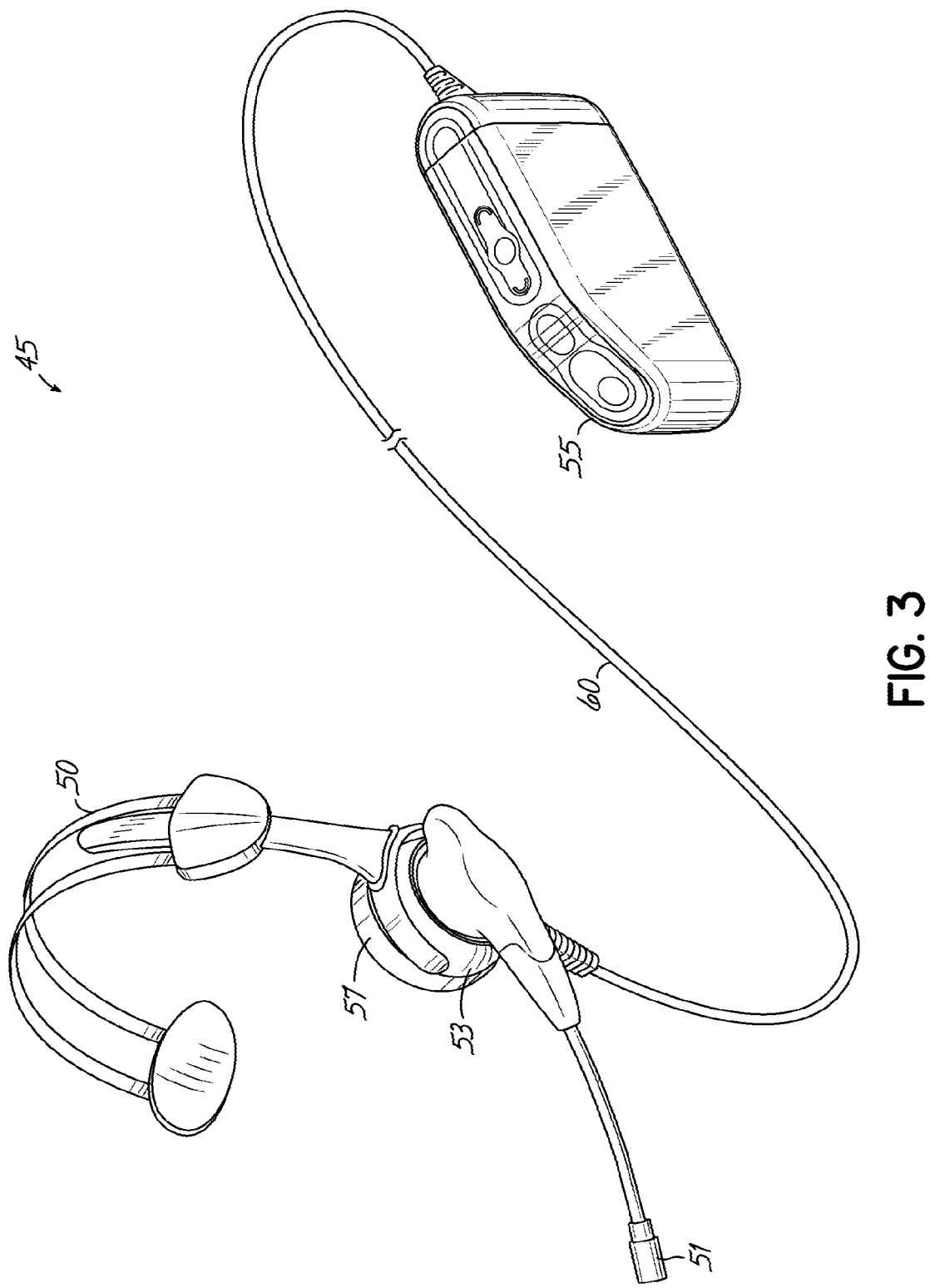
FIG. 3 is a side perspective view of one embodiment of a voice assistant of the voice assistant system of FIG. 1A consistent with the principles of the present invention.

Although the voice assistant 45 shown throughout the Figures has multiple different portions, the voice assistant 45 may represent and/or include practically any networked appliance, device, or computer as described hereinabove. An exemplary voice assistant 45 with a headset portion (or "headset") 50, a device portion (or "portable computer portion") 55, and a connecting portion such as a cable 60 that couples the headset portion 50 to the device portion 55 is illustrated in FIG. 3. In alternative embodiments, the headset 50 is coupled to the device portion 55 through a wireless link, which may also be referred to as a "connecting portion." In a further alternative embodiment, the functionality of the device portion 55 may be incorporated into the headset 50 such that voice assistant 45 is one self-contained piece of equipment.

The voice assistant 45 may also include at least one database to store data received from the voice transaction manager 35. Furthermore, Situational Awareness Questions, as discussed below, may be answered by speech dialog utilizing the data in the database, and the data in the database may also be utilized to generate a speech dialog for certain commands (e.g., a "Review" command) and to store data from the user with respect to other commands (e.g., a "Document" command). The speech dialog may include at least one statement generated by the voice assistant 45.

In some embodiments, the voice assistant 45 is a mobile device, such as a wearable computer and/or a personal digital assistant (PDA) that includes WLAN capabilities. Alternatively, the voice assistant 45 may be a voice appliance that is deployed to perform specific functions for the CNA via a main menu associated with the voice assistant 45, instead of being deployed for a general purpose. In particular, the voice assistant 45 may be a client, and more specifically a "thick client" that is configured to perform speech recognition and speech synthesis. As such, and in some embodiments, the voice assistant 45 may be similar to a client computer.

In accordance with the principles of embodiments of the invention, each CNA at the facility 10 may have their own voice assistant 45 that they wear or carry. When a CNA connects the headset portion 50 to the device portion 55 via the connecting portion 60, or when a CNA turns the voice assistant 45 on, this may activate the voice assistant 45 and "log" the CNA on to the voice assistant system 5 (e.g., establish a connection between the voice assistant 45 and the nursing workstation 20 and/or voice transaction manager 35, as well as determine which particular CNA is logging onto the voice assistant system 5 based on an identification associated with the CNA and/or the voice assistant 45, and retrieve data associated with that particular CNA and/or voice assistant 45). In response to logging the CNA on to the voice assistant system 5, one or more items may be transferred from the voice transaction manager 35 to the voice assistant 45. These items may include the list of residents assigned to the CNA for the shift, the care plan data for all of the residents assigned to the CNA, the appropriate voice templates and/or the facility configuration information, such as, but not limited to, the list of CNAs generally assigned or logged into the current shift. Moreover, the CNA may physically carry a document (e.g., document 62 illustrated in FIG. 4) that sets forth the speech vocabulary to interact with the voice assistant 45 (e.g., including the main menu 63 illustrated in FIG. 5) in a speech dialog. In particular, the CNA may use the voice assistant 45 to interact with the main menu by selecting from the predefined parameters in the form of speech input (e.g., including Situational Awareness Questions, commands and/or other vocabulary, at least a portion of which is illustrated on the document 62). The speech recognition capabilities of the voice assistant 45 receives the speech input and utilizes the speech recognition capabilities to convert the speech input into machine readable input (e.g., data that can be processed by the voice assistant 45 or another portion of the voice assistant system 5, including the nursing workstation 20 and/or voice transaction manager 35, for example). The speech synthesis capabilities of the voice assistant 45 may then provide output as part of the speech dialog in response to the speech input (e.g., answers to a Situational Awareness Question and/or speech dialog in response to a command and/or other vocabulary, for example). Furthermore, the voice assistant 45 may also be utilized to provide the CNA with audible tones and/or speech dialog in response to various statuses. The main menu and voice user interface (VUI) will be discussed hereinbelow in connection with FIGS. 5-11.

While the voice assistant 45 primarily operates utilizing voice interaction and a speech dialog with a CNA or other user, in one embodiment of the invention, a voice assistant 45 utilizes a Contactless Communication technology interface for engaging care plans and supplementing, and interacting with, any voice or speech dialog implemented through the voice assistant 45. More specifically, referring to FIG. 3A, the device 55 of the voice assistant 45 may be a mobile computer device, as noted.

The computer device 55 includes at least one conventional processing unit or processor 70 coupled to suitable memory 72. A processing unit is typically implemented in hardware using circuit logic disposed on one or more physical integrated circuit devices or chips and may be one or more microprocessors, micro-controllers, FPGAs, or ASICs. Memory 72 may include RAM, DRAM, SRAM, flash memory, and/or another digital storage medium, and also typically implemented using circuit logic disposed on one or more physical integrated circuit devices, or chips. As such, memory 72 may be considered to include memory storage physically located elsewhere in the server device, e.g., any cache memory in the at least one processing unit 70, as well as any storage capacity used as a virtual memory, e.g., as stored on a mass storage device 74, another computing system (not shown), a network storage device (e.g., a tape drive) (not shown), or another network device (not shown) coupled to the device 55 through at least one network interface 76 (illustrated and referred to hereinafter as "network I/F" 36) such as by way of the WLAN network 40.

The device 55 is coupled to headset 50 through an input/output device interface 78 (illustrated as, and hereinafter, "I/O I/F" 78). The interface 78 may be a wireless or wired interface. In particular, the device 55 receives speech input from a user through a microphone 51 of the headset and/or other user interface) and/or outputs speech or tones and other sounds to the user through a speaker 57 of the headset 50. Moreover, in an alternative embodiment, the I/O I/F 78 may communicate with one or more other peripheral devices 82.

As is conventional, the computer device 55 is typically under the control of an operating system 84 and executes or otherwise relies upon various computer software applications, sequences of operations, components, programs, files, objects, modules, etc., (program code) configured to be executed by processing unit 72 consistent with embodiments of the invention. For example, the speech recognition and speech synthesis functionality of the invention for providing a speech dialog with a care provider is one such application. In specific embodiments, the device 55 executes or otherwise relies on one or more applications 86 that are configured provide task messages or task instructions. Such task messages/instructions may be part of the speech dialog provided by the invention. The task messages or task instructions are used to execute a task, as discussed herein. The one or more applications 86 may also affect a database 88 within the mass storage 74. A suitable power supply 90 provides power for device 55.

In accordance with one embodiment of the invention, in order to supplement and interact with the speech dialog, device 55 incorporates a suitable circuitry for implementing a Contactless Communication Technology interface 92 that provides contactless communication operability for a voice assistant to use in obtaining information in addition to the information and data gathered through the speech dialog. For example, such Contactless Communication technology may include Near Field Communication (NFC) technology and associated circuitry or may use High Frequency radio frequency identification (HF RFID) technology and associated circuitry for implementing a contactless communication interface. The contactless communication interface 92 is appropriately coupled with processor or processing unit 70, and operates in conjunction with the applications 86 run by device 55, as described herein. As may be appreciated, in the interactions between a CNA or other user and a patient or person receiving care, it may be desirable to limit the speech dialog between the user and the voice assistant 45 so as to avoid uncomfortable situations where the status, care, and actions of the patients are spoken aloud, As such, the contactless communication interface 92 provides desired "silent" implementation for the voice assistant in order to capture information associated with the resident or associated with a care plan or care provided to a resident and to reduce some unnecessary speech dialog or avoid uncomfortable or embarrassing situations for the patient or resident. Such implementation of the contactless communication interface 92 is discussed further herein below. The contactless communication interface, in one embodiment, will operate in accordance with conventional NFC or HF RFID standards that are directed to short-range high frequency wireless communication. For example, the technology may operate at around 13.56 MHz and use magnetic coupling to power certain devices and communicate with such devices, such as a tag 93. To that end, the contactless communication interface might operate in reader mode so as to read information from devices, such as active or passive RFID tags or some other suitable tag or device 93. As such, a system using device 55 and one or more tag devices 93 may be used in the overall system of the invention to provide the benefits and functionality noted herein. The tag devices 93 will store information that is read by the contactless communication interface 92 in order to provide the noted functionality of the device 55 as described further below. Furthermore, the contactless communication interface might provide point-to-point communications between the voice assistant 45 and another device for the purpose of exchanging information. Also, the contactless communication interface 92 might operate to provide card emulation, and to act as a contactless card obtaining certain information. Other suitable contactless communication interfaces might also be incorporated in accordance with the invention. Various implementations of the contactless communication interface 92 within voice assistant 45 are disclosed herein.

Although one of ordinary skill in the art will appreciate that the voice assistant 45 may be implemented in a variety of ways (e.g., in some embodiments the voice assistant 45 includes only a headset 50 that in turn includes the functionality of the device portion 55), and one of ordinary skill will further realize that activation of the voice assistant 45 may cause transmission of the data from the voice transaction manager 35 to that voice assistant 45, it may be advantageous to utilize a thick client model and configure the speech recognition and speech synthesis capabilities in the voice assistant 45. By doing so, the voice assistant 45 may avoid placing substantial amounts of network traffic on the wireless network (e.g., WLAN) 40, LAN 30, or WAN 70 (discussed hereinbelow in connection with area 15) during documentation or other activities.

Furthermore, in the thick client model, aside from downloading the care plans from the voice transaction manager 35 to the voice assistant 45 at the start of the CNA's shift, the CNA may continue to work and document independent of whether she or he has a network connection. For instance, once this data transfer is complete, the voice assistant 45 may support documentation for the entire shift, even in the absence of a working wireless network 40. As such, it may be advantageous to configure more processing and/or bandwidth intensive activities of the voice assistant 45 (e.g., the speech recognition, processing and/or speech synthesis capabilities) in the device 45 and closer to the end users.

However, in the presence of an available network, the voice assistant 45 may receive updates, including real-time updates and near real-time updates (e.g., updates to care plans). Moreover, some or all of the speech input spoken by the CNA (e.g., speech input in response to a speech dialog or, alternatively, specific speech input not otherwise spoken in response to speech dialog) may be captured and transmitted (e.g., to the voice transaction manager 35) in real-time, near real-time and/or in a delayed manner (e.g., at the end of shift, day, and/or after a predetermined period of time) in the presence of an available network. Indeed, it is also worth noting that the voice assistant 45 may support real time paging. For example, a page may be first sent to the voice transaction manager 35 and then relayed to its final destination(s). In an alternative embodiment, voice assistants 45 may be configured communicate with each other directly via the wireless network 40 to send a page.

It is worth noting that the care plans for the residents typically remain stable from day to day and from shift to shift. For example, a resident needs to eat meals every day, go to the bathroom every day, etc. A care plan may change if the nurse makes the change at the nursing workstation 20, as the CNA cannot change the care plans on his or her voice assistant 45, as discussed above. As such, care plans may be received by the voice assistant 45 at the start of every shift and/or upon activation to reflect any changes to the care plans that occurred prior to the start of the shift and/or activation, and the care plans may be dynamically maintained throughout the shift and/or activation to include any changes.

As the CNA completes the different tasks associated with the items in the care plans, a data set reflective of the work completed by the CNA may be generated at the voice assistant 45. The data set may be utilized for various purposes. For example, the data set may be utilized to answer the Situational Awareness Questions of the CNA (e.g., the answer may be based on the data set alone or the answer may be based on the data set and the care plans), to generate a historical report, to generate an MDS (Minimum Data Set —summary of a patient's condition submitted to a governmental entity for reimbursement and quality control purposes), and/or to generate an exception report or Care Completion Report (e.g., at the nursing workstation, where the Care Completion Report is a report of care items not completed by assigned workers for each resident), among other purposes. Thus, the care plans on the voice assistant 45 are not configured to track the completed tasks or changes in response to the completion of work by the CNA. Rather, it is the generated data set that tracks completed work. Indeed, a new data set may be generated during each shift.

FIG. 1B illustrates an exemplary overview of the data flow throughout the voice assistant system 5, including the care plans, pages, etc. Key attributes of the data flow in the voice assistant system 5 at the facility level may include the external interfaces (e.g., to ADT (Admissions, Discharges and Transfers) interface, MDS and/or nurse call systems), data that is primarily manipulated through the web interfaces (e.g., a web browser at the nursing workstation 20), data that is primarily manipulated through the voice interface (e.g., the voice assistant 45, main menu 63 and/or VUI), key reports (e.g., MDS, exception reports, and/or historical reports), and/or the plan of care documentation ("Doc" in the drawing). In particular, the "Doc" illustrates the overlap between the web interface and the voice interface.

Referring back to FIG. 1A, the facility 10 may also include at least one charger 65 to charge the voice assistant 45. As illustrated in FIG. 1A, each charger 65 may charge up to five voice assistants 45. Furthermore, a least one item in the facility 10 may transmit and/or receive data via the Internet or a corporate wide area network (WAN) 70 to the offsite Vocollect Healthcare Systems, Inc. (VHS) department and/or the onsite enterprise customer IT department 15.

The offsite VHS department and/or the onsite enterprise customer IT department 15 may include a workstation for support, maintenance and monitoring (S&M&M) activities 75 as well as a server to aggregate S&M&M data and execute distributed maintenance 80. The offsite VHS department and/or the onsite enterprise customer IT department 15 may further include metrics and at least one dashboard 85 such as CliniConsole™ offered by VHS or some other operational effectiveness dashboard, an enterprise data repository that may be utilized for enterprise roll-up for enterprise customers 90 and/or at least one corporate dashboard 95. For example, the offsite VHS department may be able to remotely maintain the voice transaction manger 35, provide other remote support, and/or monitor performance of the voice assistant system 5.

In short, the voice assistant system 5 may emphasize distributed execution, but centralized platform management and data roll-up, as discussed hereinabove. Moreover, those of ordinary skill in the art will readily appreciate that other functionality may be possible as well. Those skilled in the art will recognize that the exemplary environments illustrated in FIGS. 1A-1B, 2A-2B and 3-4 are not intended to limit the present invention. Indeed, those skilled in the art will recognize that other alternative hardware and/or software environments may be used without departing from the scope of the present disclosure.

Figure 5:
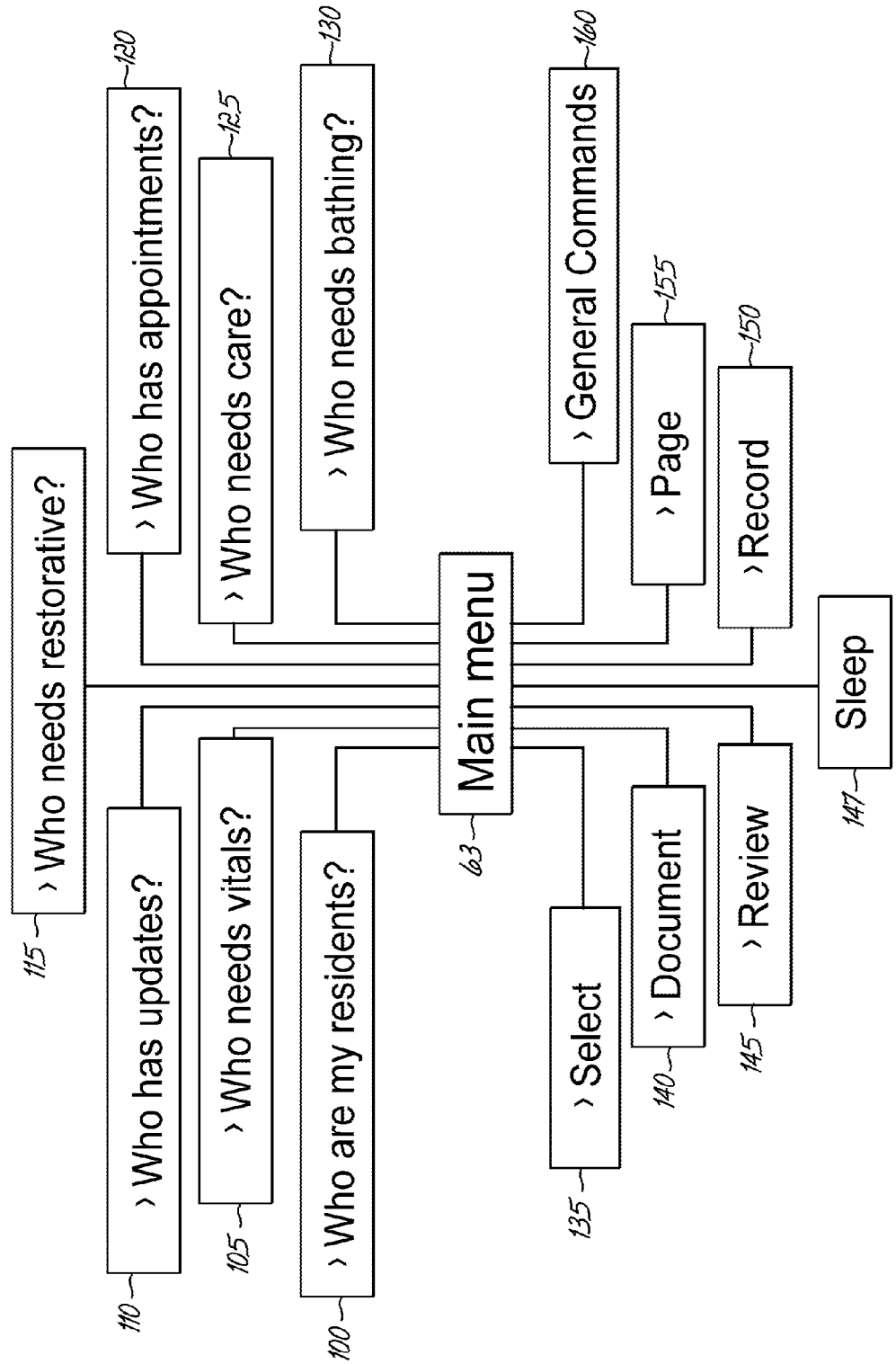
FIG. 5 is one embodiment of a main menu that a user may interact with, including selectable parameters in the form of questions and commands that the user may choose via the voice assistant of FIG. 3, consistent with the principles of the present invention.

Turning now to FIG. 5, via the main menu 63, the CNA may select at least one parameter through speech input that corresponds to a Situational Awareness Question and/or command. The speech recognition capabilities of the voice assistant 45 are utilized to receive the speech input of the user and determine the parameter selected by the CNA. A Situational Awareness Question may be utilized to query about certain situations often encountered by CNAs in their work shift such that the CNA may control their workflow with respect to various situations. For example, when a CNA faces a particular situation or is placed in a particular context, the CNA may be able to interact with the voice assistant 45 through a corresponding question and begin a speech dialog that answers the question based upon the available information. In other words, information that the CNA may need to be aware of, should be aware of, and/or needs while performing their tasks may be organized according to Situational Awareness Questions. For example, the situation or context may be related to the remaining work, time of shift (commencement of the shift, end of the shift, etc.), time of day (lunch time, snack time, etc.), current task or tasks (bathing, vitals, etc.), a particular resident the CNA is working with, a location in a facility, etc.

Various Situational Awareness Questions are illustrated as interrogatories 100-130 in FIG. 5 consistent with one embodiment of the invention. Respectively, these are, "Who are my residents?" (block 100), "Who needs vitals?" (block 105), "Who has updates?" (block 110), "Who needs restorative?" (block 115), "Who has appointments?" (block 120), "Who needs care?" (block 125), and "Who needs bathing?" (block 130). As such, these Situational Awareness Questions concern interrogatories associated with the identity of residents associated with a CNA, the identity of residents associated with a CNA that need their vitals recorded, the identity of residents associated with a CNA who have had updates made to their respective care plan, the identity of residents associated with a CNA who need one or more restorative programs, the identity of residents associated with a CNA who are in turn associated with appointments for care or other activities, the identity of residents associated with a CNA who currently need some sort of care, and the identity of residents associated with a CNA who currently need bathing. A restorative program, or restorative care, refers to activities that may help improve a resident's mobility, eating, muscle function, and the like that may be performed by a CNA. Those of ordinary skill in the art will appreciate, however, that other Situational Awareness Questions may be supported as well by the invention, for example, "What's important?", "What's different?", or "What's changed?", "What's left?", "What's scheduled?", "Who's assigned?", "What is last shift report?", among others. As such, embodiments of the invention are not limited to the specific Situational Awareness Questions and interrogatories discussed herein.

In some embodiments, the answer to each Situational Awareness Question is provided by way of a speech dialog generated by the speech recognition and synthesis capabilities of the voice assistant 45, with the answer based upon care plan information and/or other information accessed and received by the voice assistant 45. In general, the speech dialog answering the "Who" related questions will provide the names and/or room numbers of the residents that satisfy the question. In some instances, the answer may be based upon information from some or all of the care plans associated with the voice assistant 45. Furthermore, the answer may be based upon, or take into account, tasks that have already been completed. For example, if the CNA wants to know, "Who needs bathing?", it may be advantageous for the speech dialog to inform the CNA of the assigned residents that still need bathing, and not inform the CNA of assigned residents that have already been bathed by the CNA (or assigned a task that has already been completed by another CNA). As such, the answer may reflect the completion of a task by the assigned CNA or even completion of a task by another CNA, as tracked by the voice assistant system 5. For example, the CNA might ask, "Who needs care?" The voice assistant 45 may then provide a list of the residents for whom various tasks still remain. Then, through other commands, and as discussed below, the CNA may select and review the tasks for a particular resident. That is, if the answer to a Situational Awareness Question listed Mr. Smith of Room 312 as needing care (e.g., in response to the interrogatory "Who needs care?") or some specific task (e.g., in response to the interrogatory "Who needs vitals?"), the CNA may use the select command 135 to select Mr. Smith and the review command 145 to obtain information about Mr. Smith. For example, "Review vitals" may be spoken by the CNA to obtain care plan information about vitals for Mr. Smith. In some embodiments, when the CNA begins to assist an unassigned resident, the care plan for that unassigned resident is sent to the voice assistant 45.

Similarly, the answers to any questions, such as, "Who has updates?" may be based upon information associated with a particular resident that has changed and/or information associated with one or more care plans that has changed since the CNAs last login. Changes may occur because of an action by a nurse at the nursing station 20 during the CNA's shift, because of a change in the care plan of an assigned resident, because of an assignment of another resident to the CNA, etc. Moreover, there may be updates as to the facility configuration data, such as the number of CNAs currently working or logged on. As noted above in connection with FIG. 1A, updates may be sent from the nursing workstation 20 to the voice transaction manager 35 and/or to the voice assistant 45 during a shift. As such, the care plans may be dynamically maintained. Upon noting a resident with updates, the CNA can select the resident, and speak or issue a "Review updates" command for that resident.

In general, the commands may be associated with various tasks and invoked by the CNAs for assistance with, and for execution of, pending tasks. Various exemplary commands are illustrated as commands 135-160 in FIG. 5. Respectively, these are "Select" (block 135), "Document" (block 140), "Review" (block 145), "Sleep" (block 147) "Record" (block 150), "Page" (block 155) and General Commands (block 160). Furthermore, each of these commands may have additional sub-commands and/or sub-categories associated with them. For example, the "Review" command may have a sub-category for "toileting" to review the toileting of a resident. Similarly, the "Document" command may have a sub-command for "meals," the "Page" command may have a sub-command for "unit," etc. However, those of ordinary skill in the art will appreciate that additional commands other than those listed may also be supported.

For at least some commands, speech dialog is provided with the CNA that corresponds to that command. The speech dialog includes speech inputs for a user, such as a CNA and speech outputs to the user. The speech dialog may include asking the user to speak at least one input, repeating the CNAs input, etc. The speech dialog may be based upon the data in the voice assistant 45, including the care plans and/or voice templates. Such dialogs may be generated by the voice transaction manager 35 and/or the voice assistant 45 using speech synthesis as is known to a person of ordinary skill in the art. The text of the speech dialog may depend on the specific command and the data requested by the voice assistant 45, or the information to be provided by the voice assistant 45. As may be appreciated, the speech dialog could take various different forms to provide information about a resident or a care plan to a CNA, or to obtain information and data about a resident pursuant to their care plan. Thus, the invention is not limited to the specific questions or format of any given speech dialog.

Figure 6:
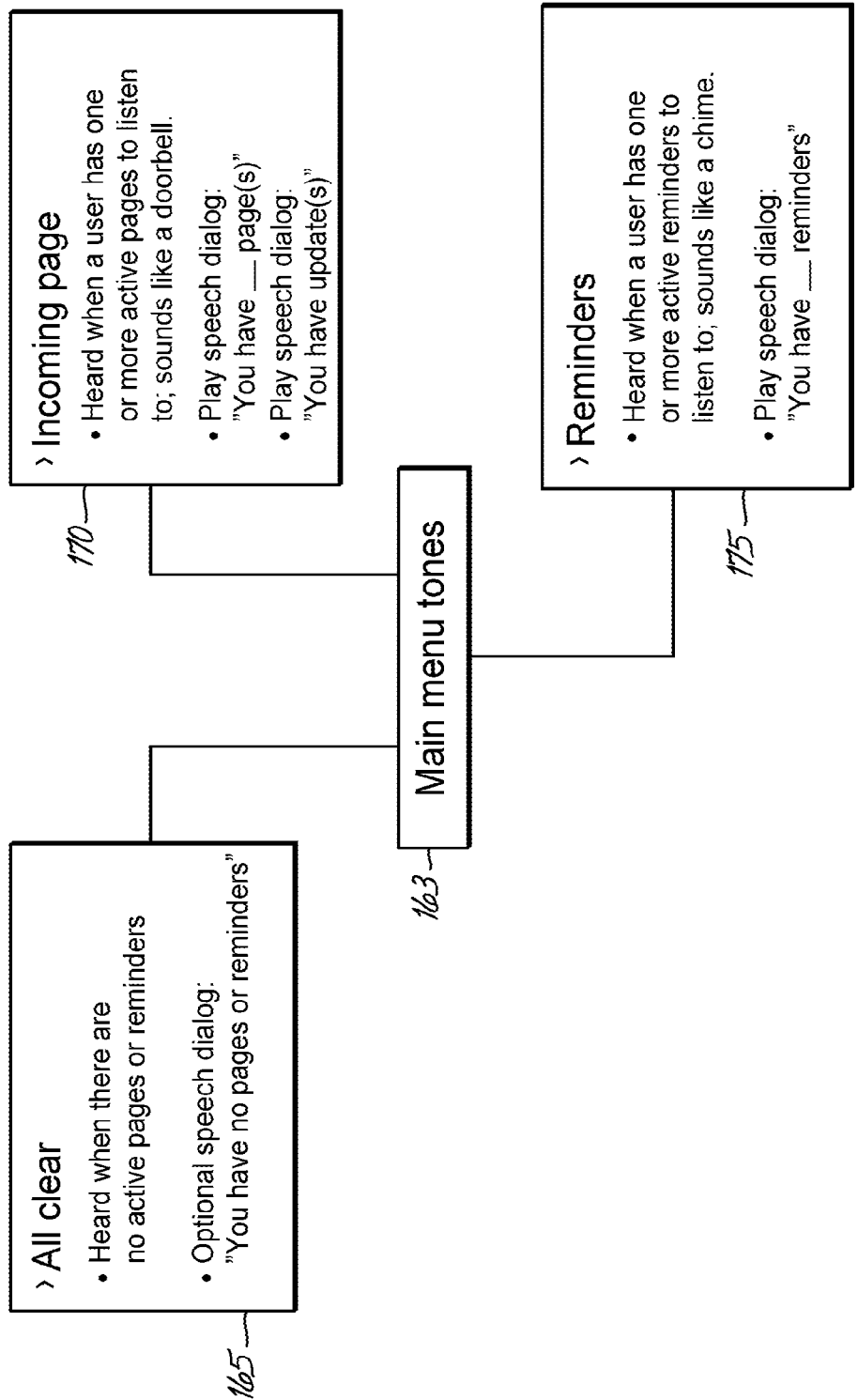
FIG. 6 illustrates main menu tones associated with FIG. 5, including tones that may be provided to the user, consistent with the principles of the present invention.

In addition to providing speech dialog in response to Situational Awareness Questions and/or commands, the voice assistant 45 may also provide a CNA with a variety of audible tones, or audible speech tones 163, as well as speech dialog in response to various statuses, as illustrated in FIG. 6. In some embodiments, such as in response to a status change (e.g., a new page and/or reminder) while the user is at the main menu, in response to a user navigating to the main menu while a page and/or reminder is outstanding (e.g., unaddressed) and/or in response to a predetermined time period elapsing while a voice assistant 45 is in the sleep mode with a page and/or reminder outstanding, an audible tone and a speech dialog associated therewith is provided, followed by another audible tone. When the CNA is not at the main menu, such as when the CNA is reviewing or documenting information, an audible tone may be provided without either the speech dialog associated therewith or the second audible tone in response to a status change. For example, an "all clear" tone 165 may be provided when there are no active pages or reminders. The "all clear" tone 165 may be followed by speech dialog that indicates "You have no pages or reminders," and that speech dialog may be followed by another "all clear" tone 165. The "incoming page" tone 170 may be provided when the CNA has one or more active pages to listen to, and may sound like a doorbell. The "incoming page" tone 170 may be followed by speech dialog that indicates "You have {N} pages," wherein "N" is the number of pages for that CNA, and that speech dialog may be followed by another "incoming page" tone 170. The incoming page may be from another CNA and may include a recorded voice message similar to a conventional voicemail. However, the page is a silent page in that a public address system (i.e., PA system) need not be utilized, leading to less disruption.

Moreover, a "reminder" tone 175 may be provided when the CNA has one or more active reminders to listen to, and may sound like a chime. The "reminder" tone 175 may be followed by speech dialog that indicates "You have {M} reminders," wherein "M" is the number of reminders for that CNA, and that speech dialog may be followed by another "reminder" tone 175. A reminder may be based upon the care plans of the assigned residents. For example, a specific task in a care plan may have to be completed at a certain time or by a certain time (e.g., preparation for an appointment), and the reminder tone 175 may be provided to the CNA to make them aware that the time has arrived or is approaching.

The audible tones and/or speech dialogs associated therewith provide audible indications to the CNA of particular information that needs attention. Therefore, rather than acting as a visual icon regarding that information, such audible tones and/or speech dialogs operate as an "earcon" to indicate to the CNA that something needs attention. Generally, a reminder earcon will be associated with time-sensitive information, such as a resident appointment that is within the care plan of a particular resident, or a time for a particular task within the care plan of that resident. For example, if a certain resident needs toileting at a particular time, a reminder earcon may be triggered to remind the CNA of the time-sensitive task. Again, the reminder earcon may include the reminder tone 175, followed by a speech dialog associated therewith, and then followed by another reminder tone 175 in response to a reminder status change while the user is at the main menu, in response to a user navigating to the main menu while there is a reminder outstanding, and/or in response to a predetermined time period elapsing while a voice assistant 45 is in the sleep mode and there is a reminder outstanding. Alternatively, the reminder earcon may include only the reminder tone 175 in response to a reminder status change when the CNA is not at the main menu, such as when the CNA is reviewing or documenting information. Through a command, such as "Review reminders" (see FIG. 8), the CNA can access the information that the reminder earcon refers to.

In accordance with another feature of the invention, rather than providing either a reminder or alert based on a particular time for when a worker is caring for or documenting a resident, the voice assistant 45 may implement the contactless communication interface 92 of the invention to engage the care plan for a resident and provide reminders, messages, and alerts. Specifically, reminders, messages, and alerts associated with a care plan for a resident might be triggered through appropriate earcons when the care provider is in proximity to the resident both temporally and spatially. That is, when the care provider is proximate to the resident, the contactless communication interface 92 is used to capture or read information from a tag associated with the resident or with the bed or with the room of a resident for the purposes of triggering a reminder, message, or alert. Once information is captured, the invention may check to see if there are any reminders, messages, or alerts that are for the resident that are associated with the captured information. If so, those reminders, messages, or alerts may be spoken to the CNA through the speech dialog so that they may be readily addressed while the CNA is with the resident. In that way, greater flexibility may be provided with respect to the workflow and care given to a resident in a timely fashion. Certain tasks may be most appropriately handled proximate to the resident, but may not have a particular time stamp or room notation associated therewith. Rather, in accordance with one feature of the invention, particular messages, reminders, or alerts may be played and tasks performed whenever a care provider conveniently finds themselves proximate to a resident.

Furthermore, the information captured using the contactless communication interface 92 may be used to indicate that a care provider provided requested care to a resident or to indicate that a care provider otherwise attended to a resident as part of their care. Part of the care plan for a resident would be to attend to the resident as they may request, in addition to the more formalized tasks of the stored care plan. Therefore, in engaging the care plan, a CNA or other care provider would answer a request. The proximity to the resident, as indicated by a scanning of a room tag by the contactless communication interface 92 to capture information, may indicate response by the CNA to a request by the resident. Specifically, residents may use a call light or other indicator to indicate to a nurse, CNA, or other care provider, that they need particular attention, that they have requested care, that they need help, or that they need to otherwise be attended to or cared for. For example, care might be requested with a call light. When a care provider enters the room and scans the room tag or some other tag associated with the room and resident to indicate proximity to the resident, any part of the care plan noting the call or request might be answered or satisfied with the capture information. Alternatively, a speech dialog is implemented to inquire if the care provider is "responding to call light?". Confirmation of the response then might also be spoken by the CNA as part of the dialog. Since the care provider, at the moment, may not otherwise be engaging through the speech dialog with a voice assistant to provide care, the contactless communication interface 92 captures information associated with the room or resident. In that way, the contactless communication interface provides a suitable silent engagement with the resident to capture information and indicate a response to a call light or response to some other request for care from that resident or to interact with the speech dialog to confirm the call or request is being answered. Thus, the captured information through interface 92 indicates that a user provided the requested care to a resident or indicates that a user attended to a resident or that the resident had their call answered. The attention indication captured through interface 92 may indicate that part of the care plan for answering a request of a resident was engaged. Alternatively, the captured information may just indicate in a general sense that the care provider was engaged with the resident, such as to talk to the resident, or provide care that the resident needed, even if not part of the formal stored care plan.

An incoming page earcon is generally triggered when there is a page that is available for the CNA. For example, if another CNA or nurse pages the particular CNA and leaves a recorded message, a page earcon may be triggered. Again, the page earcon may include the incoming page tone 170, followed by a speech dialog associated therewith, and then followed by another incoming page tone 170 in response to a page status change while the user is at the main menu, in response to a user navigating to the main menu while there is a page outstanding, and/or in response to a predetermined time period elapsing while a voice assistant 45 is in the sleep mode and there is a page outstanding. Alternatively, the page earcon may include only the incoming page tone 170 in response to a page status change when the CNA is not at the main menu, such as when the CNA is reviewing or documenting information. Through a command, such as "Review pages" (see FIG. 8), the CNA can access the information that the page earcon refers to.

In some embodiments, if a care plan has been updated, a page earcon occurs such that the CNA can be alerted to updates. In those embodiments, the page earcon includes speech dialog that indicates "You have an update." In that way, updates can be handled in a timely fashion, and the CNA can issue the command "Review updates" in response to the page earcon.

In some embodiments, earcons may be provided to the CNA when the CNA returns to the main menu and there is an outstanding page and/or reminder. Until the CNA has addressed the information or tasks associated with a particular page or reminder, the respective earcon associated therewith will be provided each time that CNA returns to the main menu. However, if a page or reminder status changes multiple times while that CNA is not at the main menu, such as when the CNA is reviewing or documenting information, the respective single tone earcon is provided once. For example, if a CNA receives two pages while that CNA is reviewing or documenting information, the respective page earcon (which includes only the incoming page tone 170, as the CNA is not at the main menu) is provided when the first page is received but not when the second page is received. Moreover, the timing of when an earcon is provided is determined intelligently. For example, if the voice assistant 45 is waiting for speech input from the CNA, an earcon may be delayed until such time as that speech input has been received but before another wait for additional speech input and/or speech dialog. In some embodiments, providing earcons while the CNA is not at the main menu is a configurable option. As such, earcons, and particularly earcons that include a tone, associated speech dialog, and the tone a second time, may not be provided outside of the main menu and/or the sleep mode.

In regard to the sleep mode, an earcon may be played after a predetermined time while a voice assistant 45 is in the sleep mode when there is a page and/or reminder outstanding. For example, when there is a page and/or reminder outstanding and when the voice assistant is in the sleep mode 45, a corresponding earcon may be provided about every 80 seconds. It will be appreciated by one having ordinary skill in the art that the corresponding earcon (e.g., for a page and/or reminder) may be played more or fewer than about every 80 seconds while the voice assistant is in sleep mode.

Those of ordinary skill in the art will appreciate that other tones, speech dialogs, and/or earcons (including sequences of tones and/or speech dialogs in earcons) may also be supported, and that many variations are consistent with the embodiments of the invention. For example, CNAs may be able to set their preferences regarding the tones/speech dialogs/earcons that are provided, when those tones/speech dialogs/earcons are provided, whether or not to remind about a task, etc. Moreover, a CNA may prefer to not be interrupted while performing a task, and as such, if the CNA is interacting with the system but away from the main menu, any tones, speech dialogs and/or earcons to be provided may be postponed until after the CNA completes the interaction in an effort to avoid interrupting the CNA and to avoid the perception of vocally directing the CNA. Indeed, consistent with the principles of the present invention, the voice assistant 45 seeks to minimize the interruptions to the CNA, and instead, the tones, speech dialogs and/or earcons may simply indicate that there is a reminder or a page for the CNA to listen to and make the reminders and pages available for the CNA to listen to via the main menu 63 when the CNA desires. As such, if the CNA is busy or otherwise unable to listen to a reminder, for example, because they are with a resident, the CNA may listen to the reminder later on as desired and constant interruptions may be reduced.

Therefore, embodiments of the invention provide near real-time voice messaging as a communication mechanism without undesired interruption. The voice user interface provides information about the workflow of the CNA and the appropriate times for the CNA to be interrupted. The voice user interface provided by embodiments of the invention slots the notification into the workflow when appropriate using audible earcons, which may include audible tones, speech dialogs or combinations thereof. Thus, information about the status of communications is conveyed without disruption of a workflow.

Figure 7:
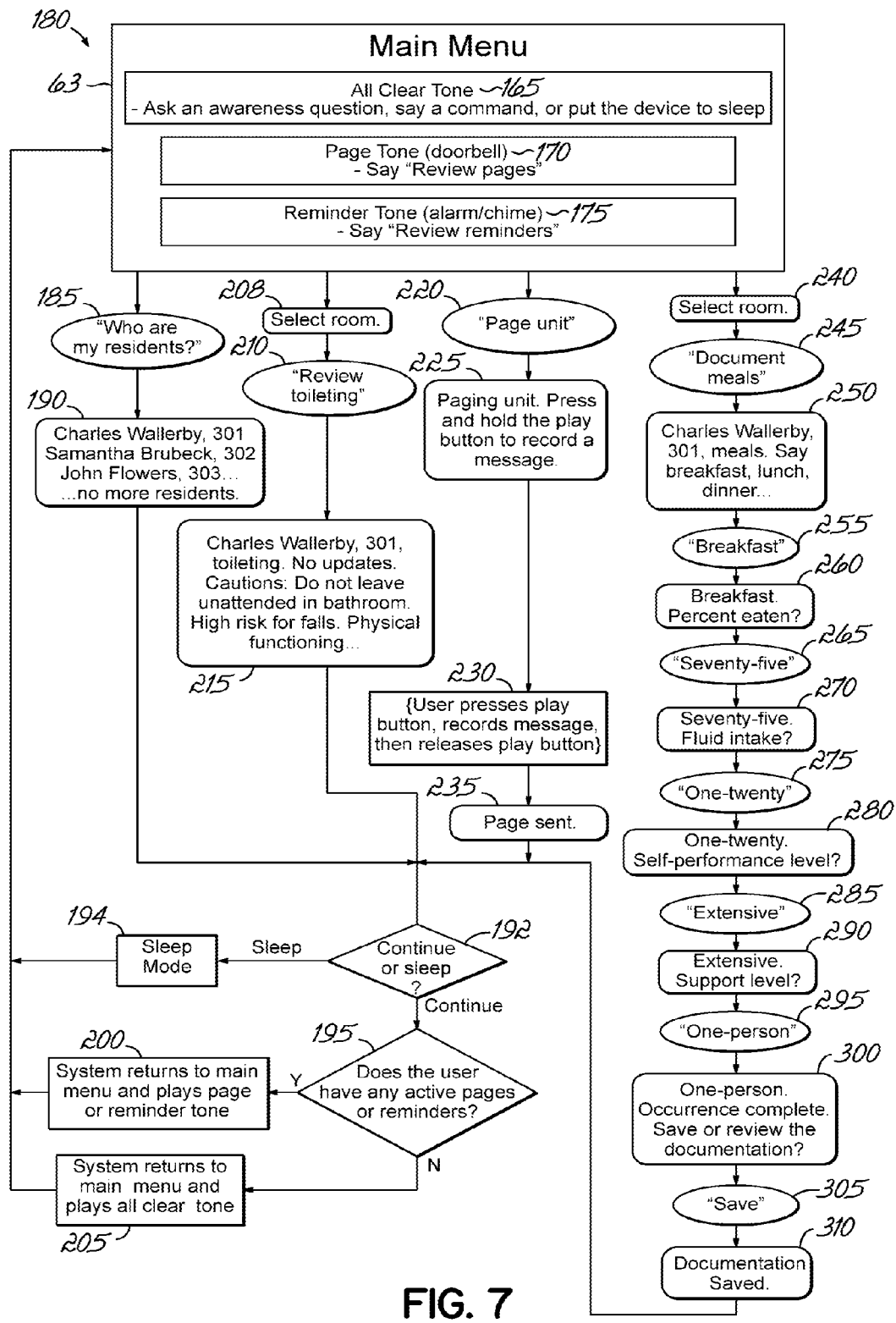
FIG. 7 is an exemplary main menu routine executed by the voice assistant system of FIG. 1A consistent with the principles of the present invention.

Turning now to FIG. 7, that figure illustrates an exemplary voice dialog and workflow routine 180 executed by the voice assistant system 5 depicting interaction between the CNA and the main menu 63. First, the CNA logs on and the care plans of the assigned residents and the facility configuration data, as well as any other pertinent data, may be sent to the voice assistant of the CNA as explained hereinabove. After logging on, the CNA may hear the all clear earcon indicating that there are no active pages or reminders, and the CNA may "sit" in the main menu 63 of the voice dialog until the CNA desires to ask a Situational Awareness Question, say a command, or put the voice assistant 45 to sleep. While the CNA sits in the main menu 63, the voice assistant 45 may be awake and using its speech recognition capabilities to actively listen for speech input, interpret the speech input and/or determine if the CNA has spoken a valid parameter that is used in the voice dialog of the invention. The CNA may put the voice assistant 45 to sleep when the CNA wants to speak (e.g., to a resident) but does not want the voice assistant 45 to use its speech recognition capabilities and other functionalities. In some embodiments, the voice assistant 45 enters a sleep mode after a predetermined time during which it is idle (e.g., including at the main menu 63), such as, for example, about 20 seconds.

When the CNA decides to ask a Situational Awareness Question, the CNA may say that Situational Awareness Question in block 185. For illustration; the voice or speech input of the CNA is illustrated in blocks in the form of ovals, the speech dialog (e.g., generated speech) from the voice assistant 45 is illustrated in blocks in the form of rounded rectangles. Returning back to block 185, the CNA may ask, "Who are my residents?" In response to the Situational Awareness Question, the CNA may be provided with the speech dialog in block 190, indicating the name and room number of each assigned resident, such as, "Charles Wallerby, 301; Samantha Brubeck, 302; John Flowers, 303 . . . no more residents".

Next, control may pass to block 192 to determine if the CNA desires to continue to the main menu 63 or put the voice assistant 45 to sleep. Specifically, the voice assistant 45 may provide a speech dialog that asks "Continue or sleep?" When the CNA chooses to put the voice assistant 45 to sleep ("Sleep" branch of decision block 192), the CNA may use the "Sleep" command (FIG. 8) to enter a sleep mode as shown at block 194. In the sleep mode, the voice assistant 45 may continue to determine whether there is at least one page and/or reminder outstanding, but otherwise wait to detect a button press of a button of the voice assistant 45 to continue converting speech input into machine readable input. In the sleep mode, the voice assistant 45 may provide an earcon corresponding to a page and/or reminder in response to receiving a page and/or reminder. That earcon may be repeated every 80 seconds. Upon exiting sleep mode (block 194), the voice assistant may proceed to the main menu 63.

When the CNA wants to continue by using a "Continue" command ("Continue" branch of decision block 192), control may pass to block 195 to determine if the CNA has any active pages and/or reminders. If there is at least one active page and/or reminder ("Yes" branch of decision block 195), control may then pass to block 200, and the voice assistant 45 may return to the main menu 63 as well as provide the page earcon and/or the reminder earcon when there is at least one outstanding page and/or reminder, respectively. When there is not at least one outstanding page and/or reminder ("No" branch of decision block 195), control may pass to block 205, and the voice assistant 45 may return to the main menu 63 as well as provide the all clear earcon. Upon returning to the main menu 63, the CNA may issue a command to the voice assistant, and may say "Review pages" if the CNA hears the page earcon or say "Review reminders" if the CNA hears the reminder earcon. The voice assistant 45 may then play the respective dialog regarding a page or reminder, respectively. After the pages or reminders have been reviewed, the all clear earcon may be provided.

To continue the example, the CNA may decide to perform tasks associated with one of the residents (in the context of this example, which is not intended to limit embodiments of the invention, Charles Wallerby). As such, the CNA may choose from a variety of voice user interface parameters in the form of commands. In particular, the CNA may select a resident, and may say, "Select Room 301" (block 208), which is Charles Wallerby's room number.

In accordance with another embodiment of the invention, voice assistant 45 may use its contactless communication interface 92 for capturing or obtaining identification information associated with a resident. Such resident identification information may be used for engaging or accessing a care plan associated with the resident by supplementing the speech dialog with non-spoken information or interacting with the speech dialog with non-spoken information. That is, information captured with interface 92 may be used as a silent "Select" command to select a resident for further engaging the care plan for the resident. For example, the room number for a particular resident might be captured with interface 92. Specifically, suitable NFC tags, such as RFID tags, might be installed near to the door of a resident's room. Such tags might be associated with labels that are installed near the doors and would contain information about the room, such as a room number. Also, tags might be on a bed or on a bracelet worn by the resident. The tags may also be programmed appropriately with the name of the resident occupying the room, for example, "Mrs. Smith", or the information tag might be linked through memory to Mrs. Smith and the care plan for Mrs. Smith. When the tags with identification information are installed in the room, with each new resident, they are appropriately associated with the resident occupying the room and the resident's care plan, such as through a database. The resident name information and any other identification information and related care plans associated with that resident are stored or maintained such as in a nursing work station 20, or elsewhere, in accordance with the invention. For example, when a tag is installed, the tag might be scanned using the voice assistant and contactless communication interface 92, and the user might then speak the room, the bed number, or other particular information directly into the voice assistant. The tag identification information read from the tag is then associated with a particular room or bed number and the resident therein. If two or more residents are within the same room, there might be a separate tag or label for each of a "bed 1" and a "bed 2". Each of those beds might be associated with a particular resident such as "Mrs. Smith" and "Mrs. Jones".

Figure 3A:
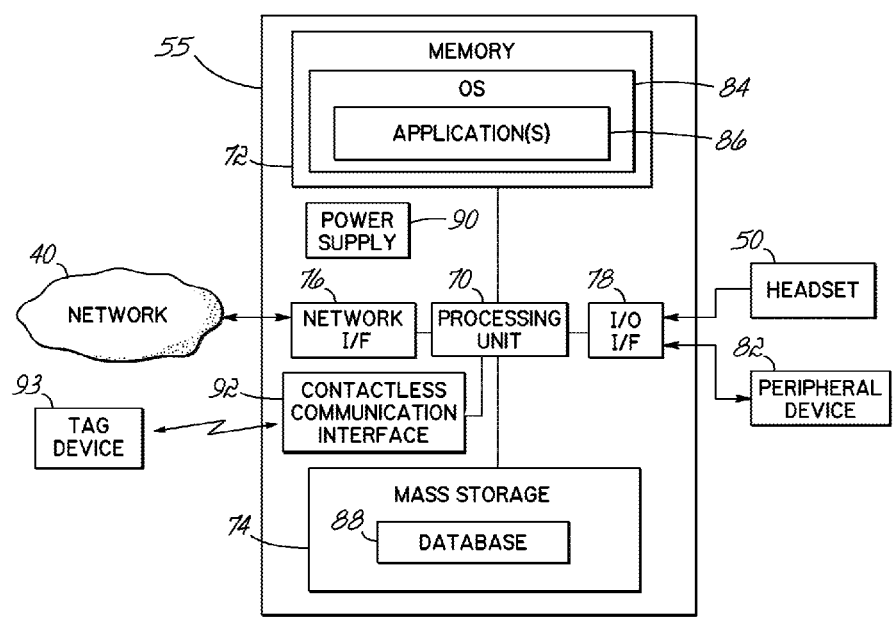
FIG. 3A is a block diagram of hardware of an embodiment of a voice assistant consistent with the invention.

When a care provider approaches the room, they may not want to impersonally refer to the room number as if the resident is just a number in the system. In accordance with the embodiment of the invention as illustrated in FIG. 3A, when a caregiver approaches a room, they move the voice assistant device 55 close enough to an applicable tag so that the contactless communication interface 92 may capture the resident information. The tag, for example, may be associated with "Room 212, Bed 1". By bringing the device 55 in close proximity, the contactless communication interface 92 captures the associated information from any tag. The captured information, and the additional information in the system associated therewith, can then be used for engaging a care plan for the resident associated with the captured information. For example, the voice assistant applications and a care plan can be engaged, as if the particular room number, bed number, and/or name of the resident were spoken in the speech dialog, even though it was not. Thus, the captured information supplements or interacts with the speech dialog, but does so silently. The invention implements data from the contactless communication interface, directly or indirectly with the speech dialog provided by the voice assistant 45, for engaging the care plan so that the care provider can proceed more quickly and more effectively, without stopping to speak a particular room number, resident name and otherwise make a verbal selection to engage the care process.

Dignity for the resident is an important aspect of long-term care and other care facilities. As such, it is desirable to not make the resident feel like a number or just one person among a large number of people within a facility. To that end, in accordance with one aspect of the present invention, the information captured or gathered by the contactless communication interface 92 may be utilized within the speech dialog to inform the care provider of the identity of the resident and to further engage the care plan for that resident. For example, when the information is captured with interface 92, after determining the resident associated with a particular room number or a particular bed within a room associated with the room number, the name of the resident may be spoken to the care provider by providing speech output through the speech dialog. The care provider is silently (at least to the resident) made aware of the name of the resident and can then use the spoken information through the speech dialog to further engage a care plan associated with a resident or a particular room number as discussed herein. Also, as noted above, using the captured information from the contactless communication interface, the program may engage various other aspects of an interaction with the resident and resident care plan according to the invention, such as prompting for what work is to be done as part of the care plan for the resident in the room, getting any messages regarding the resident, or documenting the care that is provided for the resident. In that way, the captured information may act as a "Select" command and allows the care provider to further access information and engage a care plan for the selected resident.

The CNA may then further request information regarding the care for that resident that was identified through the contactless communication interface or otherwise selected, for engaging the care plan. For example, "Review toileting" (block 210) might be spoken. When the CNA reviews certain information from the care plan, it may be read or spoken to the CNA, including the checked fields in the care plan (e.g., FIGS. 2A, 2B). For example, the CNA may be provided with speech dialog in block 215 based on the care plan of a resident and/or other information on the voice assistant 45. For example, this speech dialog may be "Charles Wallerby, 301, toileting. No updates. Cautions: Do not leave unattended in bathroom. High risk for falls. Physical functioning . . . " (block 215). As such, once a resident selected using the speech dialog or silently with the captured information from the contactless communication interface, the speech dialog provides information about the resident's care plan and assists the CNA by warning the CNA that Charles Wallerby should not be left unattended in the bathroom and is at a high risk for falls. Next, control may pass to the blocks 192, 194, 195, 200 or 205 as appropriate, and then to the main menu 63 as described hereinabove. As will be understood, various other care plans may be reviewed in a similar fashion. The voice assistant 45 thus interacts with the various care plans as necessary as directed by the CNA. As will be appreciated, the speech dialog resulting from the various commands and/or Situational Awareness Questions will vary based upon the fields selected in a care plan and other information about the resident contained in the system.

An overview of what tasks remain within a shift may be obtained by the CNA by utilizing a Situational Awareness Question of, "Who needs care?" 125. The CNA is provided with a list of the residents who still need various care procedures, or for whom certain tasks are still outstanding. Then, knowing such information, the CNA can then select a particular resident for their attention. For example, a resident could be selected, and then the command "Review care" 145 will indicate to the CNA what tasks or care procedures still remain for that particular resident.

Alternatively, the CNA may say, "Page unit" (block 220), and may be provided with the speech dialog in block 225 stating, "Paging unit. Press and hold the play button to record a message." Next, the CNA may press a play button on the voice assistant 45 to begin recording, record the message, and then release the play button as indicated in block 230, and the page may be sent to all of the employees in the unit in block 235 wearing voice assistants 45. Control may then pass to blocks 192, 194, 195, 200 or 205 as appropriate, and then to the main menu 63 as described hereinabove. It will be appreciated that, in some embodiments, pages may be sent to less than all employees in a unit wearing a voice assistant 45. As such, pages may be selectively addressed to one, or a subset of (e.g., one, some or all), all those wearing a voice assistant.

To complete tasks for a resident and document those tasks, the CNA may say "Select Room 301" (block 240), which is Charles Wallerby's room number, and then "Document meals" (block 245). As such, the CNA may be provided with speech dialog that corresponds to the "Document meals" command, such as that illustrated in blocks 250, 260, 270, 280, 290, 300, and 310. Specifically, block 250 acknowledges the intentions of the CNA to document meals and indicates the predetermined vocabulary that the CNA may say when documenting a meal by stating "Charles Wallerby, 301, meals. Say breakfast, lunch, dinner . . . " After the CNA says "breakfast" (block 255), block 260 acknowledges the documentation of breakfast and requests the CNA to indicate the percentage eaten by Charles Wallerby by stating "Breakfast. Percent eaten?" The CNA may respond with "Seventy-five" (block 265) and may then hear "Seventy-five. Fluid intake?" (block 270). The CNA may respond to this request with "One-twenty" (block 275) and may then hear "One-twenty. Self-performance level?" (Block 280). The CNA may respond with "Extensive" (block 285) and may then hear "Extensive. Support Level?" (Block 290). The CNA may respond with "One-person" (block 295) and may then hear "One-person. Occurrence complete. Save or review the documentation?" (Block 300). In that way, various data associated with a particular task is handled and documented by the voice assistant. It will be appreciated that alternative values other than those illustrated and described herein may be documented without departing from the scope of embodiments of the invention.

As may be appreciated, other data associated with other care plan segments may be captured in similar fashion with other appropriate voice dialogs that are reflective of the particular care plan and the fields therein. For example, "Document hygiene" may have a voice dialog associated with that portion of the care plan.

The self-performance and the support levels generally refer to the amount of assistance that the resident needed, and may vary based upon the activity. The different self-performance levels and support levels that the CNA may say are illustrated in document 62 in FIG. 4, along with the Situational Awareness Questions and commands that the CNA may say. Next, the CNA may say "Save" (block 305) and may then hear "Documentation saved." (block 310). Control may then pass to the blocks 192, 194, 195, 200 or 205 as appropriate, and then to the main menu 63 as described hereinabove.

Figure 8:
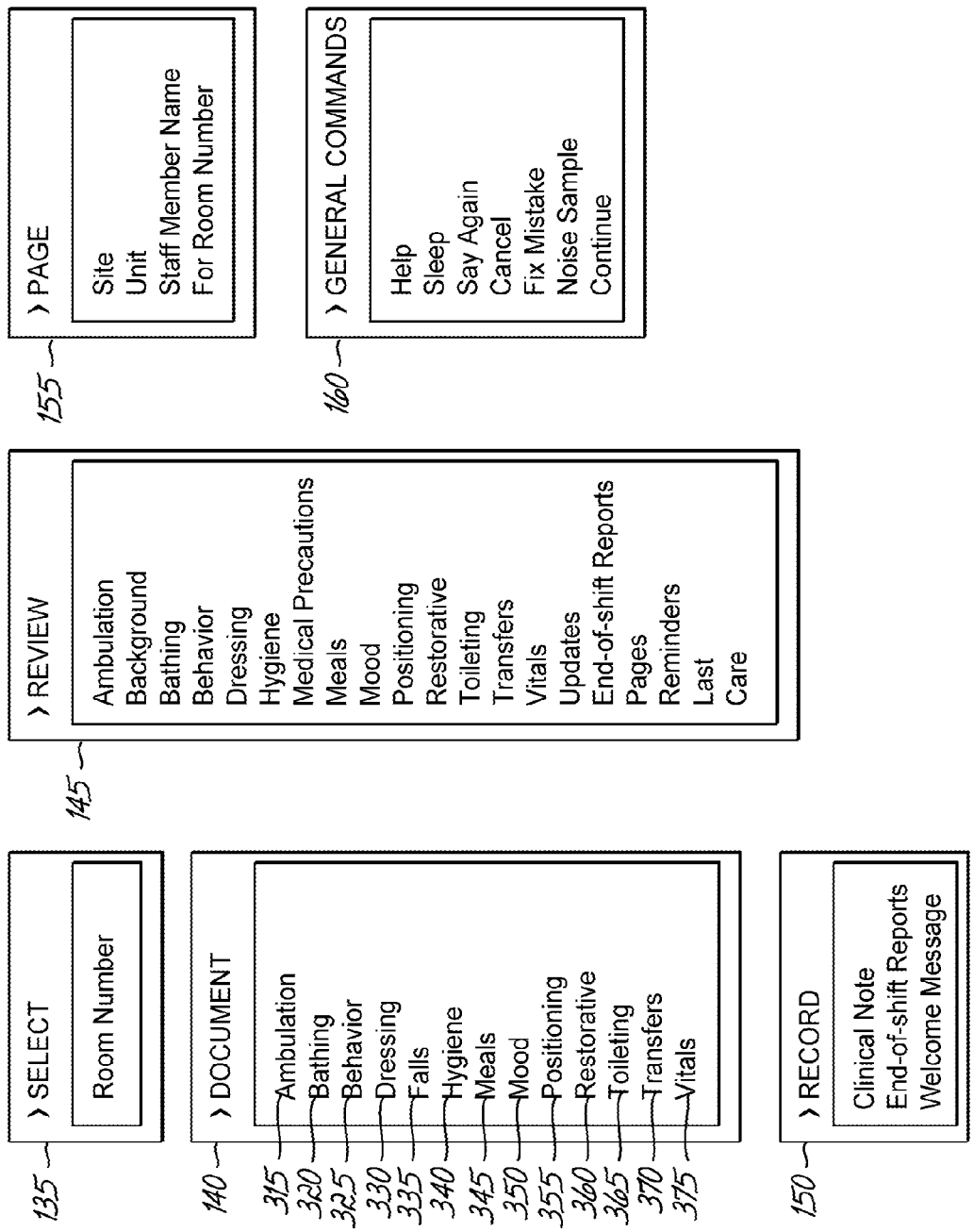
FIG. 8 is a detailed view of the parameters in the form of commands from the main menu of FIG. 5 consistent with the principles of the present invention.
Figure 9:
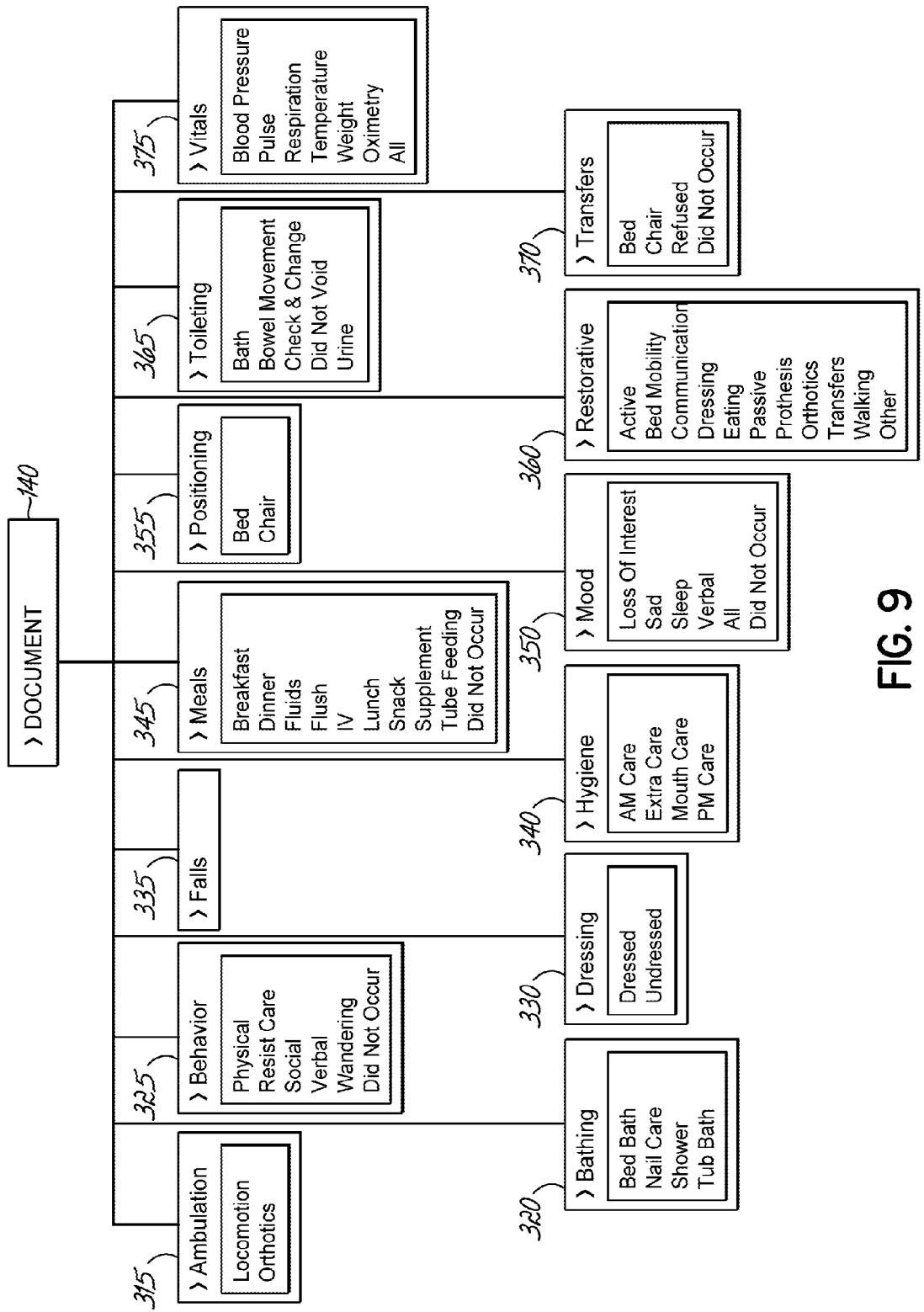
FIG. 9 is a detailed view of the document command from FIG. 8 consistent with the principles of the present invention.

Turning now to FIGS. 8-9, these figures illustrate in more detail some of the commands, sub-commands, and information that the CNA may choose via the main menu 63. One of ordinary skill in the art will appreciate that the commands and sub-commands are utilized to facilitate discussion related to the embodiments of the invention and are consistent with the principles of the present disclosure but not otherwise intended to be limiting. Similarly, one having ordinary skill in the art will appreciate that the information that may be chosen by the CNA in response to the speech dialog provided is also not intended to be limiting. FIGS. 8-9 are merely illustrative of details of various items, with the hierarchy from broadest to narrow being command, sub-command, and information. Furthermore, those of ordinary skill in the art will appreciate that each command and sub-command combination may be associated with a separate executable routine and may provide different speech dialog as necessary to facilitate the task. For instance, many command and sub-command combinations were already illustrated in connection with the blocks 210, 220, and 245 in the routine 180 in FIG. 7, and although illustrated as a single routine 180, each one of these may be a separate routine with at least one speech dialog.

Turning to FIG. 8, the "Select" command 135 may be utilized to select a room number, and then the "Document" command 140 or the "Review" command 145 may be chosen by the CNA. Starting with the "Document" command 140, a variety of tasks indicated by the various resident care plans may be performed by the CNA and documented via the "Document" command 140 and the sub-commands that correspond with that task. Some of the sub-commands are illustrated under the "Document" command 140. The sub-commands may be, but are not limited to, "ambulation" 315, "bathing" 320, "behavior" 325, "dressing" 330, "falls" 335, "hygiene" 340, "meals" 345, "mood" 350, "positioning" 355, "restorative" 360, "toileting" 365, "transfers" 370, and/or "vitals" 375. Various of the sub-commands correspond to the care plans, as discussed herein with respect to FIGS. 2A-2B and 12-22. And each one of these sub-commands may have information for the CNA to choose, as illustrated in FIG. 9. For example, the CNA may choose the "Document" command 140 and the "ambulation" sub-command such that the CNA is prompted by speech dialog associated with the combined "Document ambulation" commands to choose between locomotion or orthotics for documentation purposes (FIG. 9). Next, the CNA may be provided with the appropriate speech dialog based upon whether locomotion or orthotics was chosen. Such a speech dialog may, for example, consist of a series of questions for the CNA to answer as set forth in the example of FIG. 7.

In another example, the CNA may choose the "all" term as illustrated in FIG. 9 to document all of the information for a certain sub-command, like "vitals" 375 or "mood" 250. Also, in some instances, the CNA may have to choose the "did not occur" terminology to affirmatively document that a task did not occur (e.g., "meals" 345 or "transfers" 270), or the "did not void" terminology for "toileting" 365 to indicate that the resident did not have to go to the bathroom (see FIG. 9).

Returning to FIG. 8, each of the sub-commands (and tasks) listed under "Document" command 140 may also be utilized with the "Review" command 145 such that the CNA may review any of these portions of the care plan during his or her shift. The CNA may additionally review "medical precautions," "updates" (e.g., to a care plan), "end-of-shift reports" (e.g., recorded by the nurses indicating information that the CNA should be aware of), "pages," "reminders," "last" (e.g., last weight, last urine, last bowel movement, last meals, last vitals, last fluids, etc.) and/or "care" (e.g., to see what tasks are outstanding for a resident).

Next, the CNA may also use the "Record" command 150 and the "clinical note" sub-command to record a clinical note. In particular, the clinical note may be recorded to inform a nurse of a problem or indicate some other observation of the CNA. Upon recording the clinical note, the clinical note may be transmitted from the voice assistant 45 of the CNA to the nursing workstation 20 for the nurse to address. Additionally, the nurse may be provided with a page earcon on their own voice assistant 45 to indicate that a clinical note has been received. As such, this process may ensure that the nurses address each clinical note recorded and that the corresponding care plan is updated as needed at the workstation 20 by the nurse.

Furthermore, with respect to the "Record" command 150, the sub-command of the "end-of-shift reports" and "welcome message" may be reserved for the nurses. In particular, a nurse may utilize the "end-of-shift reports" sub-command to record the reports during or after a meeting with the CNAs at the end of the shift, for example, in order to inform the CNAs scheduled for the next shift of anything that they should be aware about. The "welcome message" sub-command may be utilized to record a message that is sent to everyone with a voice assistant 45. An audible earcon, such as a page earcon, may alert a CNA to such a welcome message.

In addition to documenting certain information regarding the care given to a resident using a speech dialog, in accordance with another aspect of the invention, the contactless communication interface of the voice assistant may provide additional documentation information or data via a read or scan, rather than through voice and the speech dialog. That is, the contactless communication interface is used to supplement the speech dialog for documenting tasks. Engaging the care plan for a resident includes documenting information associated with the execution of the care plan and the care provided. The contactless communication interface captures information to further provide information for documenting. For example, if any medications are offered to be taken by the resident, the voice assistant may be utilized to document that particular medication information. The medications used might be associated with RFID tags or other tags, such as on their containers. The containers might be brought in close proximity to the voice assistant 45 such that the contactless communication interface 92 may read the information and verify the medications immediately at the point of care. Other information, such as equipment used for therapy purposes, might also be captured readable tags, which are available for the equipment. For example, information might be captured as a documented part of the case plan where the resident is taken to therapy. The captured information can then be used in the documenting of the care.

Figure 10A:
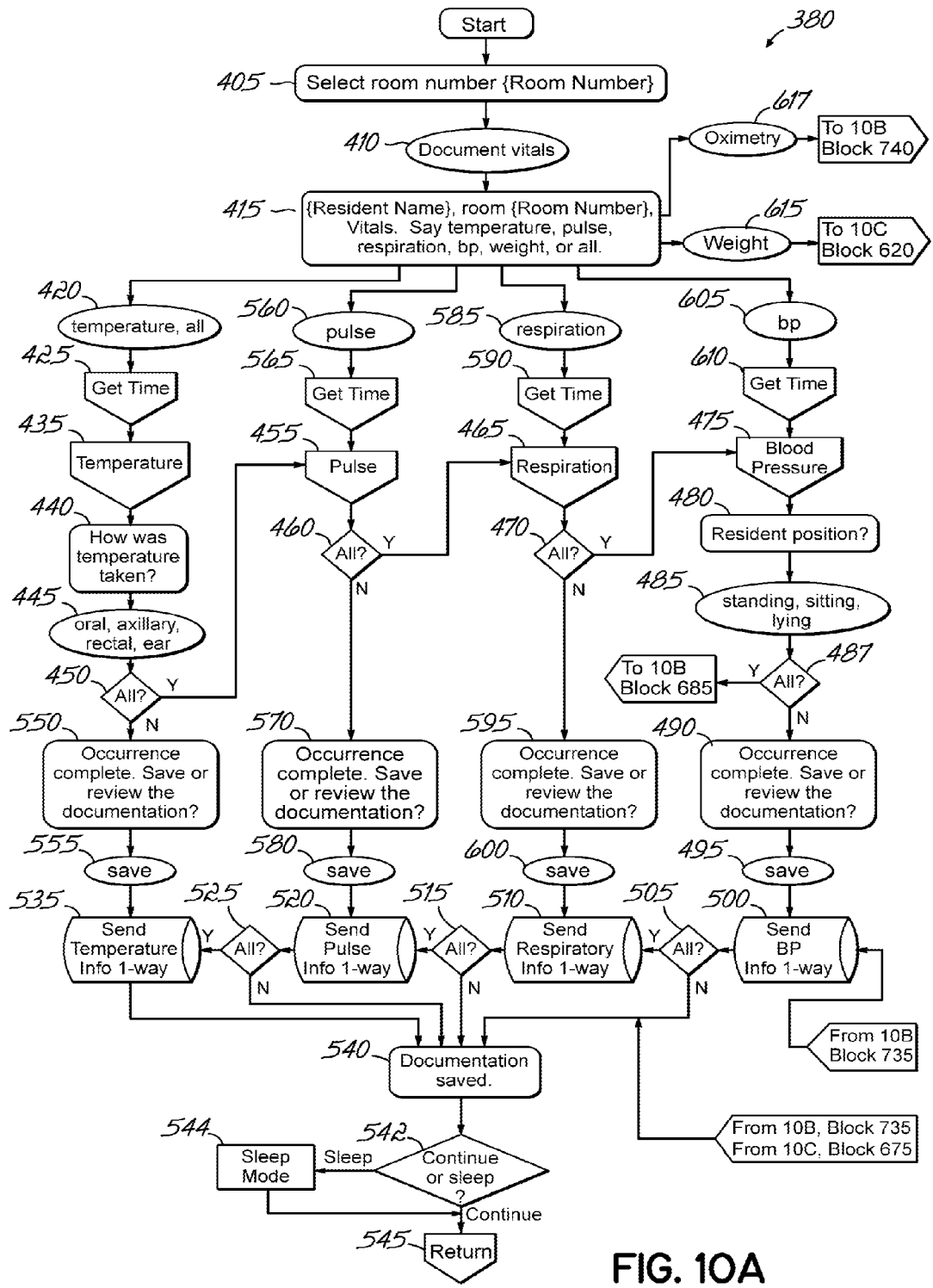
FIGS. 10A-10B are an exemplary documentation of a vitals routine executed by the voice assistant system of FIG. 1A consistent with the principles of the present invention.

In accordance with another aspect of the invention, the captured information that is used for documenting might initiate a speech dialog associated with the captured information. For example, similar to the various speech dialogs that are implemented for the subcommands, such as illustrated in FIG. 10A, a speech dialog might be implemented associated with the medication dispensed at the point of care. Cautions and any additional work flow related to medications taken by the resident can be presented by voice speech upon information captured through the contactless communication interface with respect to the medication. The information captured by interface 92 thus initiates a speech dialog related to the captured information. There may be other medical information about the resident or resident care that might also be captured using the contactless communication interface 92. Thus the invention is not limited to capturing just medication information for documentation purposes.

Although the CNAs may be restricted in their ability to utilize these sub-commands, a CNA may utilize the "Page" command 155 and the sub-commands associated therewith to page the site, to page a unit, to page a particular staff member by using the staff member's name and/or to page for a room number. Furthermore, the CNA may choose the "General" command 160 and sub-commands listed below it to request help with acceptable terminology that the CNA may say, place the voice assistant 45 to sleep and/or have the voice assistant 45 repeat the last speech dialog or say again. Moreover the CNA may utilize the sub-commands listed under the General Commands 160 to cancel, fix a mistake and/or to perform a sample of the background noise of the current environment.

FIGS. 10A-10C and FIG. 11 illustrate an exemplary documentation routine. As discussed in connection with FIG. 9, various vitals might be documented along with other information. Referring to FIG. 10A, the exemplary routines may include a documentation of vitals routine 380, a weight analysis routine 390 (which may be, in turn, included in the documentation of vitals routine 380), and a weight routine 400 (which may be, in turn, included in the weight analysis routine 390), respectively. The routine 380 assumes that the CNA chose the "Document" command 140, the sub-command "vitals" 355, and the additional sub-command "all". As such, the exemplary routine 380 may be executed and may call routines 390 and 400 during its execution. As before, the CNA's speech input is illustrated in ovals while speech dialog from the voice assistant 45 is illustrated in rounded rectangles.

Figure 10B:
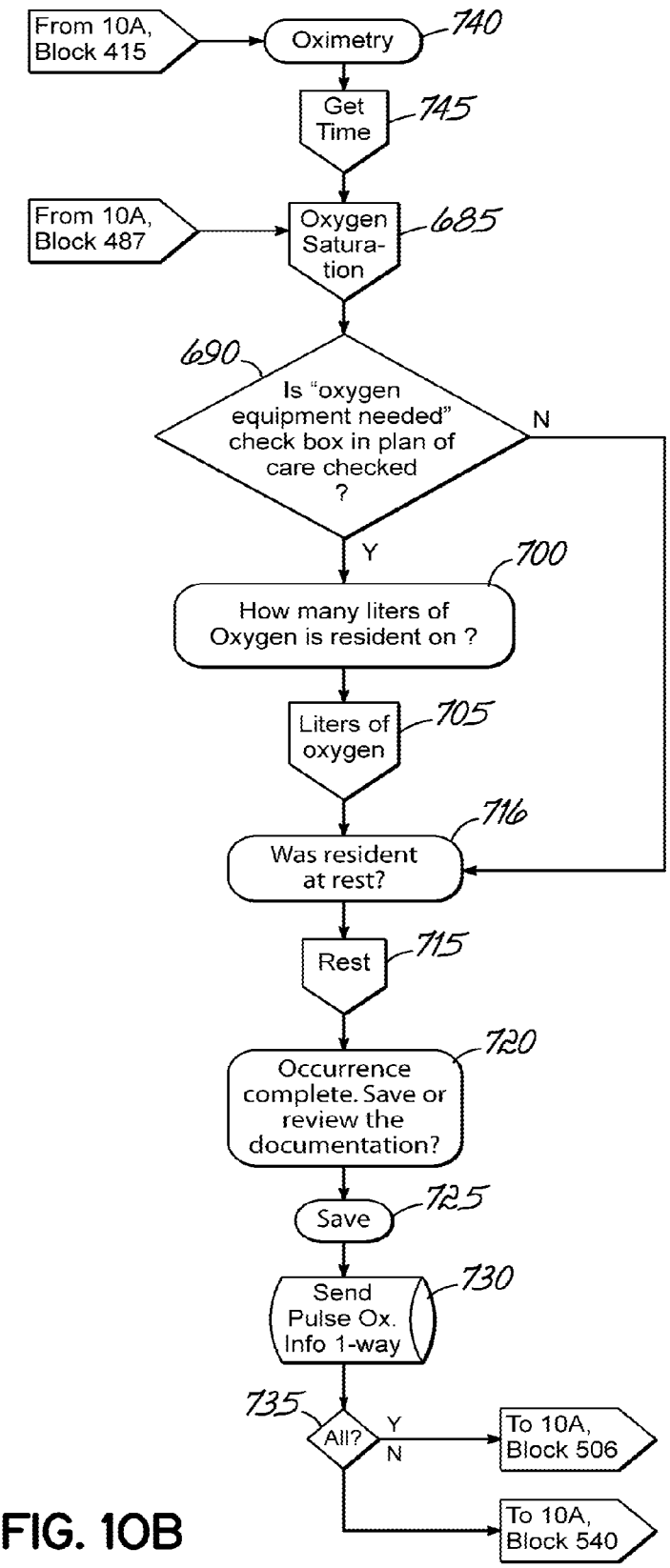
Figure 10C:
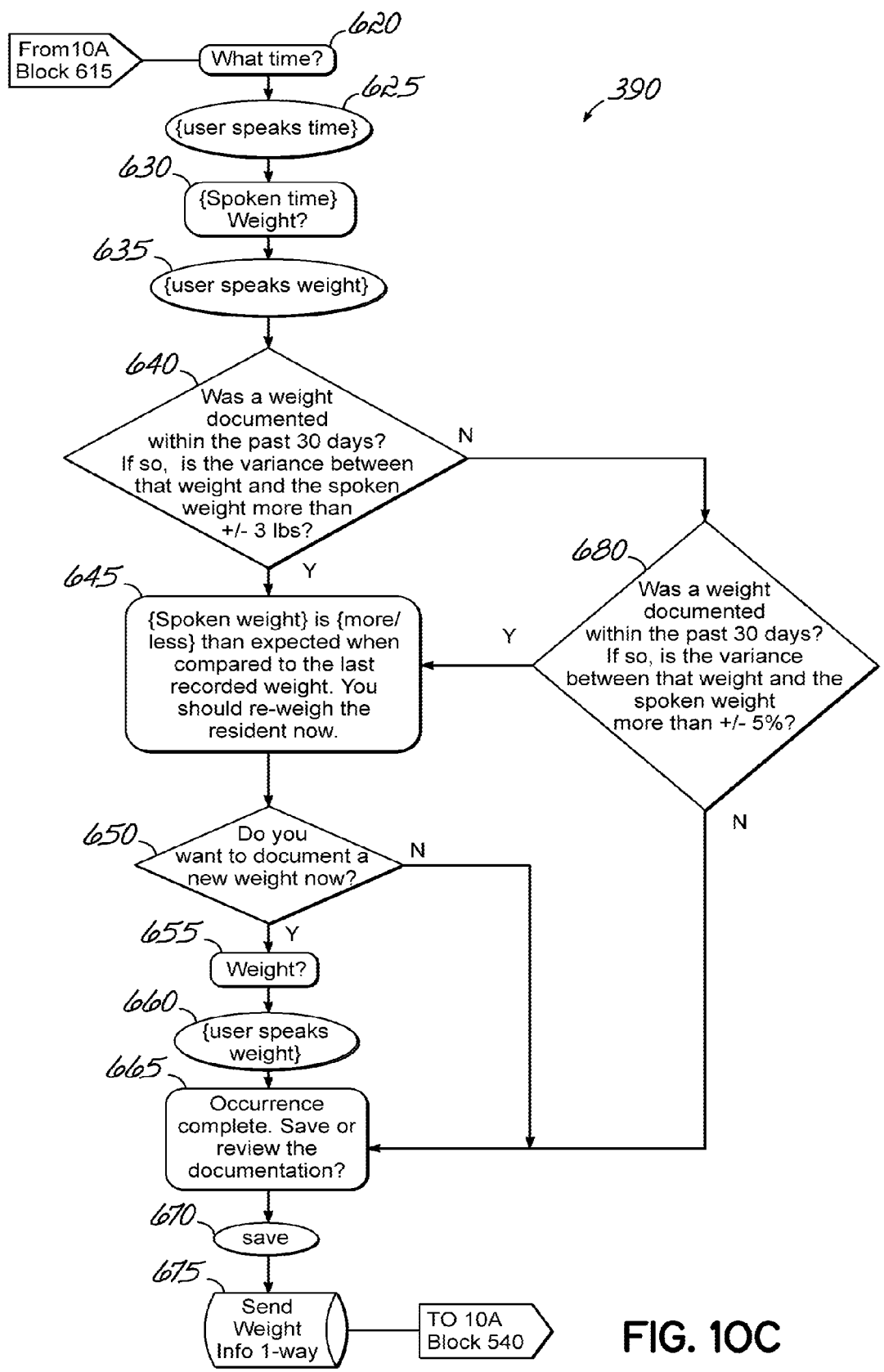
FIG. 10C is an exemplary weight analysis routine that may be called from the documentation routine of FIGS. 10A-10B, and that is also executed by the voice assistant system of FIG. 1A consistent with the principles of the present invention.

Turning to FIGS. 10A-10C and routine 380, when the CNA decides to engage in tasks related to the vitals of a resident, the CNA may say "Select room {Room Number}" (block 405), with the "Room Number" insert being the room number of the resident. The CNA may then say "Document vitals" (block 410). Upon receiving these commands, the voice assistant 45 may say "{Resident Name}, room {Room Number}, Vitals. Say temperature, pulse, respiration, BP, oximetry, weight, or all," (Block 415). The CNA may choose any of the vitals individually and the appropriate path may be followed in the speech dialog via routine 380, but in this example, the CNA chooses to document "all" vitals (block 420). As such, control may pass to block 425 to get the time.

In some embodiments, block 425 may call a "get time" routine to determine and verify the current time. Specifically, the "get time" routine may determine a time then provide that time to the CNA through a speech dialog to verify. Alternatively, the CNA may be provided with speech dialog requesting they speak the time. Next, control may pass to block 435 to call a temperature routine to determine the temperature of the resident. Block 440 may ask the CNA to state "How was the temperature taken?", and the CNA may say "oral," "axillary," "rectal," or "ear" (block 445).

When the CNA indicates that all the vitals are to be documented ("Yes" branch of decision block 450), control may then pass to block 455 to call a pulse routine to document a pulse of the resident and then to block 460 and block 465 for other vitals. The block 465 may call a respiration routine to document a respiration of the resident, and then to block 470 and block 475, with block 475 calling a blood pressure, or "bp," routine to document a by of the resident. Next, the CNA may be asked to provide the position of the resident when the blood pressure was taken at block 480. The CNA may say standing, sitting, or lying (block 485), and then control may pass to block 487 and block 685, with block 685 calling for an oxygen saturation, or "oximetry," routine to document a pulse-oxygen level of the resident. Next, the system may check to see if an "oxygen equipment needed" check box in a care plan is checked (block 690). When the check box is checked ("Yes" branch of decision block 690) the CNA may be asked how many liters of oxygen the resident is on (block 700). The CNA may then indicate the number of liters of oxygen the resident is on (block 705). After documenting the number of liters of oxygen the resident is on (block 705) or if the system determines that the check box for indicating whether oxygen equipment needed is not checked ("No" branch of decision block 690), the CNA may be asked whether the resident was at rest (block 710). The CNA may then indicate whether the resident was at rest or not (block 715), and then control may pass to block 720 to state "Occurrence complete. Save or review documentation?" When the CNA states "save" (block 725) control may pass to block 730 to send the pulse oximetry information one way (e.g., to the voice transaction manager 35). Likewise, control may pass to blocks 735, 500, 505, 510, 515, 520, 525, and 535 to send the blood pressure information, respiration information, the pulse information, and the temperature information one way for storage. Next, control may pass to block 540, which states "Documentation saved", and then to block 542 to determine whether to continue or sleep. When the CNA indicates to put the voice assistant to sleep ("Sleep" branch of decision block 542) the voice assistant may enter a sleep mode (block 544). When the CNA chooses to continue ("Continue" branch of decision block 542) and/or after the sleep mode (block 544), the voice assistant may return to the main menu (block 545).

However, if the CNA chooses to individually document the temperature, for example, control may pass through items 450, 550, 555, 535, 540, 542, 544 and/or 545, as previously described. If the CNA only wants to document the pulse, control may flow from block 415 through the path that includes items 560, 565, 455, 460, 570, 580, 520, 525, 540, 542, 544, and/or 545. If the CNA only wants to document the respiration, control may flow from block 415 through the path that includes items 585, 590, 465, 470, 595, 600, 510, 515, 540, 544, and/or 545. Moreover, if the CNA only wants to document the blood pressure, control may flow from block 415 to items 605, 610, 475, 480, 485, 490, 495, 500, 505, 540, 544, and/or 545. Similarly, if the CNA only wants to document oximetry, control may flow from block 415 to items 617, 740, 745, 685, 690, 700, 705, 710, 715, 720, 725, 730, 735, 540, 544, and/or 545.

It is worth noting that in the illustrated routine 380, weight was not one of the vitals that was documented when the CNA indicated that they wanted to document "all," but those of ordinary skill in the art will appreciate that in other embodiments, weight may be included when the CNA chooses to document all. As such, attention will now turn to documentation of the weight. Starting with block 415, if the CNA only wants to document the weight of the resident (block 615), control may pass to the weight analysis routine 390 and the appropriate speech dialog as illustrated in FIG. 10C.

Figure 11:
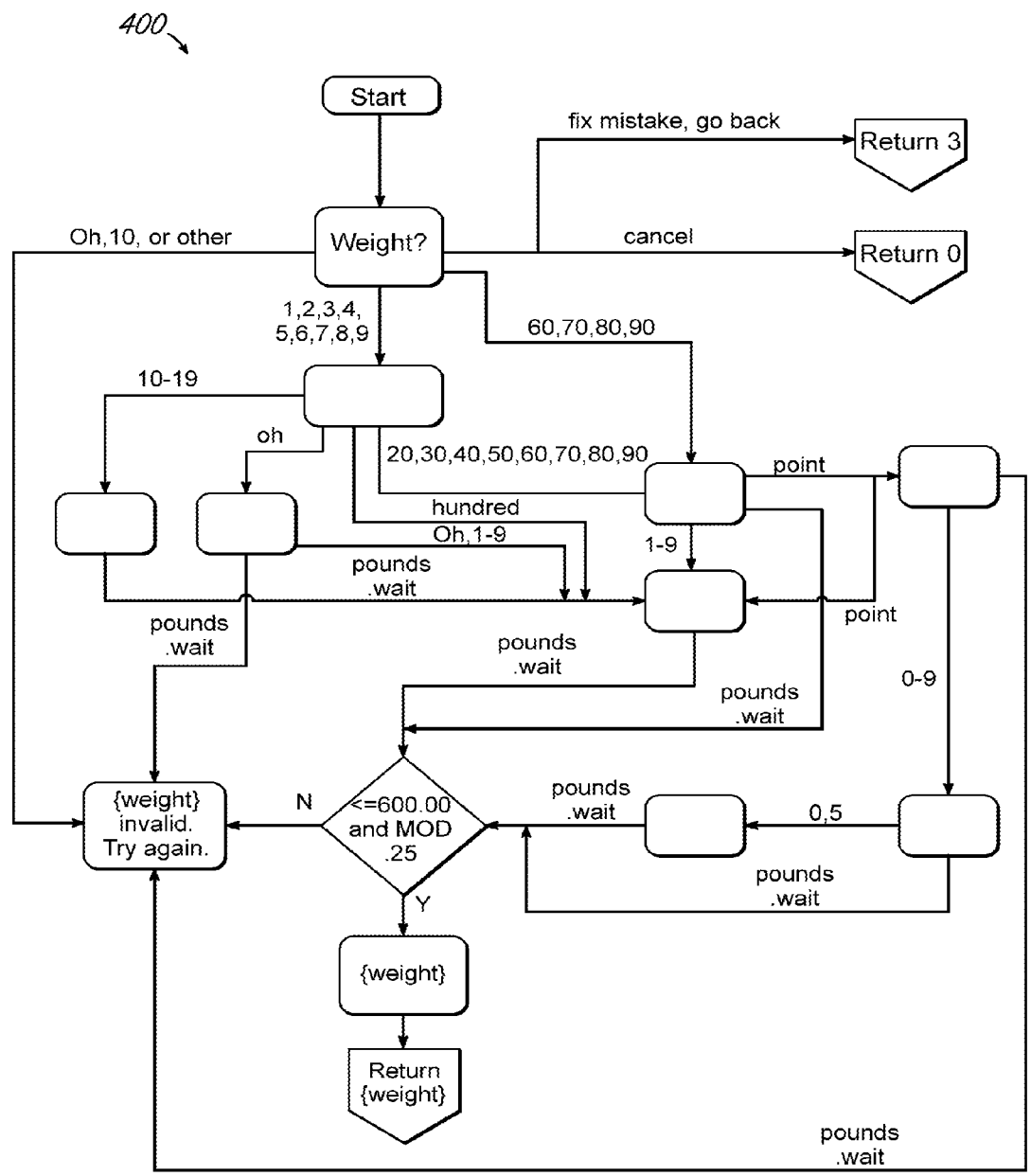
FIG. 11 is an exemplary weight routine that may be called from the weight analysis routine of FIG. 10C, and that is also executed by the voice assistant system of FIG. 1A consistent with the principles of the present invention.

As illustrated in FIG. 10C and the weight analysis routine 390, block 620 may ask the CNA for the time, and the CNA may speak the time at block 625. Next, block 630 may repeat the spoken time and ask the CNA for the weight, and the CNA may speak the weight as noted at block 635 (which may be obtained from a scale used to weigh the resident). In the corresponding exemplary weight speech recognition routine 400 as shown in FIG. 11, the weight is captured. In routine 400, the CNA's speech is illustrated on the lines, and as the CNA speaks the numbers, different paths are traversed. In particular, routine 400 illustrates a corrective routine that intelligently determines the weight of the resident based on the speech input from the CNA. For example, the weight is also checked to determine it is a valid weight, and if it is, the weight is returned to routine 390. As may be appreciated, other weight speech recognition routines might be used to capture the spoken weight.

Nonetheless, with reference once again to the routine 390, regardless of how the weight is determined, control may pass to block 640. Block 640 determines if another weight has been documented for that same resident in the past three days. If so, block 640 determines if a variance (e.g., difference, differential) between that previous weight and the spoken weight from block 635 is more than about three pounds lower or more than about three pounds higher. However, those of ordinary skill in the art will appreciate that the variance may be compared to other preselected values consistent with the principles of the present invention, and may be based on, for example, best practices.

If the variance is about three pounds lower or about three pounds higher, control may pass to block 645 to indicate to the CNA that the spoken weight is more or less than expected when compared to the last recorded weight. Moreover, the block 645 also indicates to the CNA that he or she should re-weigh the resident now. Next, control may pass to block 650 to determine if the CNA wants to document another weight, and if so, control may pass to items 655 and 660 to receive another weight, such as per routine 400. The CNA may then be provided with an indication that the occurrence is complete, and asked whether to save or review the documentation at block 665. After the CNA says "save" (block 670), control may pass to block 675 to send the weight information one way (e.g., to the voice transaction manager 35), and then back to routine 380 in FIGS. 10A-10B for the nurse assistant to inform the CNA that the documentation has been saved (block 540), to determine whether to continue or sleep (block 542), to enter a sleep mode (block 544) and/or to proceed to the main menu (block 545).

Returning to block 640 in routine 390 in FIG. 10C, if a weight was not documented within the last three days, control may pass to block 680 to determine if a weight was documented within the past 30 days. If so, block 680 determines if a variance between the current weight and the weight of the past 30 days has more or less than about a five percent differential. If the differential is about five percent, control may pass to block 645 for the voice assistant to suggest to the CNA that the resident should be re-weighed, as previously discussed. Otherwise, control may pass to block 665, as previously discussed.

Those of ordinary skill in the art may appreciate that by immediately analyzing the weight for the CNA, by comparing the weight the CNA is entering to the previously entered weight at the point of care (e.g., at the scale), the CNA may be able to avoid documenting an erroneous weight, and may immediately weigh the resident again and provide a new weight. This presents a significant time savings in resident care, because normally an improper weight would not be noticed until significantly later and would require a duplicated, time consuming, and possibly difficult and intrusive effort to get the resident re-weighed. The present invention provides verification right at the point of care. Alternatively, if the weight is correct but lower than it should be, for example, the CNA may immediately learn about the lower weight and inform a nurse (e.g., by recording a clinical note and/or page). In turn, the nurse may adjust a care plan of the resident, including adding warnings that the resident may be at a high risk for falls due to the lower weight, as needed. Indeed, those of ordinary skill in the art will appreciate that with the immediate weight analysis provided by the invention, the CNA may be assisted with weighing a resident and may learn about an anomalous weight thereof at the point of care to avoid having to transport the resident to the scale again for re-weighing days or weeks later. Rather, the appropriate actions may be taken immediately for a correct but possibly anomalous weight.

The contactless communication interface 92 of voice assistant 45 also provides an ability to track possessions of residents within a facility. Generally, a long-term care facility, such as a nursing home, is unique in that the staff are accountable for the well-being of the people therein. This implies that it is their task to keep track of the resident's possessions, such as clothing and other possessions while they are continually on the move in the confined spaces of the facility. In accordance with one aspect of the invention, the particular items for a resident are tagged. The voice assistant has the ability to read information from the tag with the contactless communication interface, and to supplement a speech dialog in accordance with aspects of the invention for informing the care provider as to the ownership of the item. The item might be found during an ongoing speech dialog. Or, may be found at another time. The voice assistant may automatically provide the possession information and implement any associated speech dialog upon bringing the item in proximity to the voice assistant. Alternatively, a care provider may initiate the dialog by asking, "Whose is this?" or some other similar inquiry as to the ownership of a particular item. As such, the contactless communication interface provides the ability to further enhance the care provided to the residents in accordance with the invention by providing the return of the item to a resident.

While the present invention has been illustrated by the description of the embodiments thereof, and while the embodiments have been described in considerable detail, it is not the intention of the application to restrict or in any way limit the scope of the appended claims to such detail. Additional advantages and modifications will readily appear to those skilled in the art. Therefore, the invention in its broader aspects is not limited to the specific details or representative apparatus and method, and illustrative examples shown and described. For example, the principles of the present invention may be adapted for a setting different than a nursing home. Accordingly, departures may be made from such details without departure from the spirit or scope of applicant's general inventive concept.

The invention claimed is:

1. A method of providing care to a resident using at least one mobile device comprising:
    receiving at least one individualized care plan for a resident, a care plan defining a plurality of tasks to be performed by a user for providing care to a resident, the at least one individualized care plan identified at least in part by the at least one mobile device automatically reading a contactless communication tag associated with the resident, the at least one mobile device comprising a contactless communication interface configured to automatically read the contactless communication tag as a user of the mobile device approaches the resident;
    storing the received care plan on the mobile device;
    capturing speech inputs from the user through the mobile device;
    providing speech outputs to the user through the mobile device;
    using the speech inputs and speech outputs and providing a speech dialog with the user through the mobile device, the speech dialog being reflective of a stored care plan for a resident;
    capturing non-spoken information associated with a resident with a contactless communication interface;
    capturing additional non-spoken information as a background noise sample; and
    using the captured information and the captured speech inputs for engaging the care plan.

2. The method of claim 1, comprising:
    determining if the mobile device can connect to an available network;
    if the mobile device can connect to an available network, connecting the mobile device to the available network and transmitting the captured information, captured speech input, and/or stored care plan over the available network; and
    if the mobile device cannot connect to an available network, storing the captured information, storing the captured speech input, and/or updating the stored care plan.

3. The method of claim 1, comprising:
    determining if the mobile device can connect to an available network;
    if the mobile device can connect to an available network, connecting the mobile device to the available network and receiving updates via the available network.

4. The method of claim 1, comprising:
    determining if the mobile device can connect to an available network;
    if the mobile device can connect to an available network, connecting the mobile device to the available network and receiving updates to at least one care plan via the available network.

5. The method of claim 1, comprising:
    determining if the mobile device can connect to an available network;
    if the mobile device can connect to an available network, connecting the mobile device to the available network and receiving real-time updates via the available network.

6. The method of claim 1, comprising:
    determining if the mobile device can connect to an available network;
    if the mobile device can connect to an available network, connecting the mobile device to the available network and transmitting the captured information, captured speech input, and/or stored care plan over the available network in near real-time and/or in a delayed manner.

7. The method of claim 1, further comprising receiving an indication comprising a speech output from a speaker associated with the at least one mobile device based at least in part on the contactless communication interface reading the contactless communication tag associated with the resident, the indication comprising the resident's name and/or at least one task associated with the individualized care plan.

8. The method of claim 1, wherein the speech inputs reflect the user addressing the resident by name and/or the user performing the at least one of the plurality of tasks.

9. An apparatus, comprising:
    a microphone for capturing speech inputs from a user;
    a speaker for providing speech outputs to the user;
    a contactless communication interface configured to automatically read a contactless communication tag;
    a processor;
    a memory; and
    program code resident in the memory and configured to be executed by the processor to assist a user with providing care to a resident at least in part by:
    storing at least one care plan in the memory for a resident, the care plan defining a plurality of tasks to be performed by a user to provide care to the resident;
    receiving an indication comprising a speech output from the speaker based at least in part on the at least one care plan, the indication comprising the resident's name and/or at least one of the plurality of tasks to be performed by the user, the at least one care plan identified at least in part by the contactless communication interface automatically reading a contactless communication tag associated with the resident;

using the speech inputs and speech outputs to provide a speech dialog with a user that is reflective of a care plan for the resident;

capturing non-spoken information as a background noise sample; and using the captured information and the captured speech inputs for engaging the care plan.

10. The apparatus of claim 9, wherein the program code is configured to be executed by the processor to assist a user with providing care to a resident by:
    determining if the apparatus can connect to an available network;
    if the apparatus can connect to an available network, connecting the apparatus to the available network and transmitting the captured information, captured speech input, and/or stored care plan over the available network; and
    if the apparatus cannot connect to an available network, storing the captured information, storing the captured speech input, and/or updating the stored care plan.

11. The apparatus of claim 9, wherein the program code is configured to be executed by the processor to assist a user with providing care to a resident by:
    determining if the apparatus can connect to an available network;
    if the apparatus can connect to an available network, connecting the apparatus to the available network and receiving updates via the available network.

12. The apparatus of claim 9, wherein the program code is configured to be executed by the processor to assist a user with providing care to a resident by:
    determining if the apparatus can connect to an available network;
    if the apparatus can connect to an available network, connecting the apparatus to the available network and receiving updates to at least one care plan via the available network.

13. The apparatus of claim 9, wherein the program code is configured to be executed by the processor to assist a user with providing care to a resident by:
    determining if the apparatus can connect to an available network;
    if the apparatus can connect to an available network, connecting the apparatus to the available network and receiving real-time updates via the available network.

14. The apparatus of claim 9, wherein the program code is configured to be executed by the processor to assist a user with providing care to a resident by:
    determining if the apparatus can connect to an available network;
    if the apparatus can connect to an available network, connecting the apparatus to the available network and transmitting the captured information, captured speech input, and/or stored care plan over the available network in real-time.

15. The apparatus of claim 9, wherein the program code is configured to be executed by the processor to assist a user with providing care to a resident by:
    determining if the apparatus can connect to an available network;
    if the apparatus can connect to an available network, connecting the apparatus to the available network and transmitting the captured information, captured speech input, and/or stored care plan over the available network in near real-time and/or in a delayed manner.

16. The apparatus of claim 9, wherein:
    the apparatus further comprises a contactless communication interface configured to automatically read contactless communication tags; and
    the program code is further configured to be executed by the processor to assist a user with providing care to a resident at least in part by:
        automatically reading a contactless communication tag associated with the resident; and
        accessing the at least one care plan when the apparatus automatically reads the contactless communication tag associated with the resident.

17. The apparatus of claim 16, wherein the apparatus is configured to automatically read the contactless communication tag associated with the resident as the user approaches the resident.

18. The method of claim 9, wherein the indication comprising the speech output is received in near real-time as the user approaches the resident.

19. A mobile device, comprising:
    a contactless communication interface configured to automatically read a contactless communication tag as a user of the mobile device approaches a resident;
    a microphone for capturing speech inputs from a user;
    a speaker for providing speech outputs to a user;
    a network interface;
    a processor;
    a memory; and
    program code resident in the memory and configured to be executed by the processor to assist a user with providing care to a resident by:
        storing at least one care plan in the memory for a resident, the care plan defining a plurality of tasks to be performed by a user to provide care to the resident;
        retrieving an individualized care plan selected from among the at least one care plan in the memory, the individualized care plan identified at least in part by the mobile device automatically reading a contactless communication tag associated with the resident;
        receiving an indication comprising a speech output from the speaker based at least in part on the individualized care plan, the indication comprising the resident's name and/or at least one of the plurality of tasks to be performed by the user;
        using the speech inputs and speech outputs to provide a speech dialog with a user that is reflective of a care plan for the resident;
        capturing non-spoken information as a background noise sample;
        using the captured information and the captured speech inputs for engaging the care plan;
        determining if the mobile device can connect to an available network via the network interface; and
        if the mobile device cannot connect to an available network, storing the captured information, storing the captured speech input, and/or updating the stored care plan.

20. The mobile device of claim 19, wherein the program code is configured to be executed by the processor to assist a user with providing care to a resident by:
    if the mobile device can connect to an available network, connecting the mobile device to the available network and transmitting the captured information, captured speech input, and/or stored care plan over the available network.

21. The mobile device of claim 19, wherein the program code is configured to be executed by the processor to assist a user with providing care to a resident by:
if the mobile device can connect to an available network, connecting the mobile device to the available network and receiving updates via the available network.

22. The mobile device of claim 19, wherein the program code is configured to be executed by the processor to assist a user with providing care to a resident by:
if the mobile device can connect to an available network, connecting the mobile device to the available network and receiving updates to at least one care plan via the available network.

23. The mobile device of claim 19, wherein the program code is configured to be executed by the processor to assist a user with providing care to a resident by:
if the mobile device can connect to an available network, connecting the mobile device to the available network and receiving real-time updates via the available network.

24. The mobile device of claim 19, the processor to assist a user with providing care to a resident by:
if the mobile device can connect to an available network, connecting the mobile device to the available network and transmitting the captured information, captured speech input, and/or stored care plan over the available network in real-time.

25. The mobile device of claim 19, wherein the program code is configured to be executed by the processor to assist a user with providing care to a resident by:
if the mobile device can connect to an available network, connecting the mobile device to the available network and transmitting the captured information, captured speech input, and/or stored care plan over the available network in near real-time and/or in a delayed manner.

* * * * *